US012564340B2

(12) United States Patent
Sowards et al.

(10) Patent No.: US 12,564,340 B2
(45) Date of Patent: Mar. 3, 2026

(54) ECCENTRIC SINGLE-CORE FIBER-OPTIC ENABLED MEDICAL DEVICE

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 521 days.

(21) Appl. No.: 17/863,211

(22) Filed: Jul. 12, 2022

(65) Prior Publication Data

US 2024/0016425 A1 Jan. 18, 2024

(51) Int. Cl.
A61B 5/1459 (2006.01)
A61B 1/00 (2006.01)
(Continued)

(52) U.S. Cl.
CPC ........ A61B 5/1459 (2013.01); A61B 1/00009 (2013.01); A61B 1/00013 (2013.01);
(Continued)

(58) Field of Classification Search
CPC .............. A61B 5/1459; A61B 1/00009; A61B 1/00013; A61B 1/00045; A61B 1/00055; A61B 1/00057; A61B 1/0661; A61B 1/07; A61B 1/126; A61B 1/3137; A61B 5/02055; A61B 5/0261; A61B 5/14539;
(Continued)

(56) References Cited

U.S. PATENT DOCUMENTS

| 3,493,288 A | 2/1970 | Oltman et al. |
| 4,768,855 A | 9/1988 | Nishi et al. |

(Continued)

FOREIGN PATENT DOCUMENTS

| CA | 3025240 A1 | 11/2017 |
| DE | 102016109601 A1 | 11/2017 |

(Continued)

OTHER PUBLICATIONS

PCT/US2022/024934 filed Apr. 14, 2022 International Search Report and Written Opinion dated Jul. 18. 2022.
(Continued)

*Primary Examiner* — Joel Lamprecht
*Assistant Examiner* — Amy Shafqat
(74) *Attorney, Agent, or Firm* — Rutan & Tucker LLP

(57) ABSTRACT

Disclosed herein are medical systems, devices, and methods for performing vascular treatments and diagnoses. A vascular device include an optical fiber including a single fiber core disposed offset from a central axis of the optical fiber. The single fiber enables logic of the system to perform determine multiple conditions of the device and the patient. The conditions may include one or more of blood flow parameters, infusate delivery parameters, location of the device within the patient, pH of the blood, oxygen level of the blood, damage to the optical fiber, or core temperature of the patient. The elongate medical device may be a catheter, a stylet, a guidewire, or a probe.

5 Claims, 12 Drawing Sheets

(51) Int. Cl.

| | |
|---|---|
| *A61B 1/06* | (2006.01) |
| *A61B 1/07* | (2006.01) |
| *A61B 1/12* | (2006.01) |
| *A61B 1/313* | (2006.01) |
| *A61B 5/00* | (2006.01) |
| *A61B 5/0205* | (2006.01) |
| *A61B 5/026* | (2006.01) |
| *A61B 5/145* | (2006.01) |
| *A61B 5/1455* | (2006.01) |
| *A61B 34/20* | (2016.01) |

(52) U.S. Cl.

CPC ...... *A61B 1/00045* (2013.01); *A61B 1/00055* (2013.01); *A61B 1/00057* (2013.01); *A61B 1/0661* (2013.01); *A61B 1/07* (2013.01); *A61B 1/126* (2013.01); *A61B 1/3137* (2013.01); *A61B 5/02055* (2013.01); *A61B 5/0261* (2013.01); *A61B 5/14539* (2013.01); *A61B 5/14552* (2013.01); *A61B 5/6852* (2013.01); *A61B 2034/2061* (2016.02); *A61B 2562/0271* (2013.01)

(58) Field of Classification Search

CPC .............. A61B 5/14552; A61B 5/6852; A61B 2034/2061; A61B 2562/0271; A61B 2562/0266; A61B 5/0084; A61B 5/6885; A61B 5/065; A61B 5/01; A61B 5/0059; A61B 5/026; A61B 5/14551; A61B 90/06; A61M 3/0204; A61M 3/0279; A61M 25/0023; A61M 25/0043; A61M 25/0082

See application file for complete search history.

(56) References Cited

U.S. PATENT DOCUMENTS

| | | | |
|---|---|---|---|
| 4,813,429 | A | 3/1989 | Eshel et al. |
| 5,099,845 | A | 3/1992 | Besz et al. |
| 5,163,935 | A | 11/1992 | Black et al. |
| 5,178,153 | A | 1/1993 | Einzig |
| 5,207,672 | A | 5/1993 | Roth et al. |
| 5,211,165 | A | 5/1993 | Dumoulin et al. |
| 5,220,703 | A | 6/1993 | Kanayama et al. |
| 5,275,151 | A | 1/1994 | Shockey et al. |
| 5,295,212 | A | 3/1994 | Morton et al. |
| 5,423,321 | A | 6/1995 | Fontenot |
| 5,454,807 | A | 10/1995 | Lennox et al. |
| 5,517,997 | A | 5/1996 | Fontenot |
| 5,599,492 | A | 2/1997 | Engelson |
| 5,622,170 | A | 4/1997 | Schulz |
| 5,633,494 | A | 5/1997 | Danisch |
| 5,693,043 | A | 12/1997 | Kittrell et al. |
| 5,740,808 | A | 4/1998 | Panescu et al. |
| 5,827,313 | A | 10/1998 | Ream |
| 5,872,879 | A | 2/1999 | Hamm |
| 5,873,842 | A | 2/1999 | Brennen et al. |
| 5,879,306 | A | 3/1999 | Fontenot et al. |
| 5,906,579 | A | 5/1999 | Vander Salm et al. |
| 5,957,831 | A | 9/1999 | Adair |
| 6,035,229 | A | 3/2000 | Silverstein et al. |
| 6,069,698 | A | 5/2000 | Ozawa et al. |
| 6,081,741 | A | 6/2000 | Hollis |
| 6,178,346 | B1 | 1/2001 | Amundson et al. |
| 6,208,887 | B1 | 3/2001 | Clarke |
| 6,210,362 | B1 | 4/2001 | Ponzi |
| 6,319,227 | B1 | 11/2001 | Mansouri-Ruiz |
| 6,343,227 | B1 | 1/2002 | Crowley |
| 6,398,721 | B1 | 6/2002 | Nakamura et al. |
| 6,485,482 | B1 | 11/2002 | Belef |
| 6,563,105 | B2 | 5/2003 | Seibel et al. |
| 6,564,089 | B2 | 5/2003 | Izatt et al. |
| 6,593,884 | B1 | 7/2003 | Gilboa et al. |

| | | | |
|---|---|---|---|
| 6,597,941 | B2 | 7/2003 | Fontenot et al. |
| 6,619,857 | B2 | 9/2003 | Miyake |
| 6,650,923 | B1 | 11/2003 | Lesh et al. |
| 6,685,666 | B1 | 2/2004 | Fontenot |
| 6,687,010 | B1 | 2/2004 | Horii et al. |
| 6,690,966 | B1 | 2/2004 | Rava et al. |
| 6,701,181 | B2 | 3/2004 | Tang et al. |
| 6,711,426 | B2 | 3/2004 | Benaron et al. |
| 6,816,743 | B2 | 11/2004 | Moreno et al. |
| 6,892,090 | B2 | 5/2005 | Verard et al. |
| 6,895,267 | B2 | 5/2005 | Panescu et al. |
| 6,975,803 | B2 | 12/2005 | Koide et al. |
| 7,043,287 | B1 | 5/2006 | Khalil et al. |
| 7,132,645 | B2 | 11/2006 | Kom |
| 7,273,056 | B2 | 9/2007 | Wilson et al. |
| 7,344,533 | B2 | 3/2008 | Pearson et al. |
| 7,366,562 | B2 | 4/2008 | Dukesherer et al. |
| 7,366,563 | B2 | 4/2008 | Kleen et al. |
| 7,396,354 | B2 | 7/2008 | Rychnovsky et al. |
| 7,406,346 | B2 | 7/2008 | Kleen et al. |
| 7,515,265 | B2 | 4/2009 | Alfano et al. |
| 7,532,920 | B1 | 5/2009 | Ainsworth et al. |
| 7,587,236 | B2 | 9/2009 | Demos et al. |
| 7,603,166 | B2 | 10/2009 | Casscells, III et al. |
| 7,699,855 | B2 | 4/2010 | Anderson et al. |
| 7,729,735 | B1 | 6/2010 | Burchman |
| 7,757,695 | B2 | 7/2010 | Wilson et al. |
| 7,758,499 | B2 | 7/2010 | Adler |
| 7,840,253 | B2 | 11/2010 | Tremblay et al. |
| 7,992,573 | B2 | 8/2011 | Wilson et al. |
| 8,032,200 | B2 | 10/2011 | Tearney et al. |
| 8,054,469 | B2 | 11/2011 | Nakabayashi et al. |
| 8,060,187 | B2 | 11/2011 | Marshik-Geurts et al. |
| 8,073,517 | B1 | 12/2011 | Burchman |
| 8,078,261 | B2 | 12/2011 | Imam |
| 8,182,433 | B2 | 5/2012 | Leo et al. |
| 8,187,189 | B2 | 5/2012 | Jung et al. |
| 8,197,494 | B2 | 6/2012 | Jaggi et al. |
| 8,267,932 | B2 | 9/2012 | Baxter et al. |
| 8,369,932 | B2 | 2/2013 | Cinbis et al. |
| 8,388,541 | B2 | 3/2013 | Messerly et al. |
| 8,571,640 | B2 | 10/2013 | Holman |
| 8,597,315 | B2 | 12/2013 | Snow et al. |
| 8,622,935 | B1 | 1/2014 | Leo |
| 8,700,358 | B1 | 4/2014 | Parker, Jr. |
| 8,781,555 | B2 | 7/2014 | Burnside et al. |
| 8,798,721 | B2 | 8/2014 | Dib |
| 8,968,331 | B1 | 3/2015 | Sochor |
| 8,979,871 | B2 | 3/2015 | Tyc et al. |
| 9,119,551 | B2 | 9/2015 | Qi et al. |
| 9,186,046 | B2 | 11/2015 | Ramamurthy et al. |
| 9,339,206 | B2 | 5/2016 | Grunwald |
| 9,339,221 | B1 | 5/2016 | Heaton, II et al. |
| 9,345,510 | B2 | 5/2016 | Patel et al. |
| 9,360,630 | B2 | 6/2016 | Jenner et al. |
| 9,549,685 | B2 | 1/2017 | Cox et al. |
| 9,560,954 | B2 | 2/2017 | Jacobs et al. |
| 9,572,492 | B2 | 2/2017 | Simpson et al. |
| 9,622,706 | B2 | 4/2017 | Dick et al. |
| 9,645,326 | B1 | 5/2017 | Sausse et al. |
| 9,649,048 | B2 | 5/2017 | Cox et al. |
| 9,678,275 | B1 | 6/2017 | Griffin |
| 9,678,284 | B2 | 6/2017 | Coggi et al. |
| 9,737,213 | B1 | 8/2017 | Heaton, II et al. |
| 9,872,978 | B1 | 1/2018 | Zaborsky et al. |
| 10,231,643 | B2 | 3/2019 | Grunwald |
| 10,231,753 | B2 | 3/2019 | Burnside et al. |
| 10,258,240 | B1 | 4/2019 | Eberle et al. |
| 10,265,133 | B1 | 4/2019 | McClellan |
| 10,327,830 | B2 | 6/2019 | Grant et al. |
| 10,349,890 | B2 | 7/2019 | Misener et al. |
| 10,448,837 | B2 | 10/2019 | Manzke et al. |
| 10,492,876 | B2 | 12/2019 | Anastassiou et al. |
| 10,551,245 | B2 | 2/2020 | Do et al. |
| 10,568,586 | B2 | 2/2020 | Begin et al. |
| 10,603,126 | B2 | 3/2020 | Karguth et al. |
| 10,620,386 | B2 | 4/2020 | Van Der Mark et al. |
| 10,631,718 | B2 | 4/2020 | Petroff et al. |
| 10,687,891 | B2 | 6/2020 | Belhe et al. |

(56) References Cited

U.S. PATENT DOCUMENTS

| | | | |
|---|---|---|---|
| 10,932,670 B2 | 3/2021 | Smith et al. | |
| 10,939,889 B2 | 3/2021 | Flexman et al. | |
| 10,992,078 B2 | 4/2021 | Thompson et al. | |
| 10,992,079 B2 | 4/2021 | Stats et al. | |
| 11,000,207 B2 | 5/2021 | Burnside et al. | |
| 11,000,265 B1 | 5/2021 | Ryu et al. | |
| 11,103,321 B2 | 8/2021 | Braun et al. | |
| 11,123,047 B2 | 9/2021 | Jaffer et al. | |
| 11,259,892 B2 | 3/2022 | Hufford et al. | |
| 11,284,916 B2 | 3/2022 | Patel et al. | |
| 11,369,342 B2 | 6/2022 | Irisawa | |
| 11,382,653 B2 | 7/2022 | Patel et al. | |
| 11,474,310 B2 | 10/2022 | Sowards et al. | |
| 11,525,670 B2 | 12/2022 | Messerly et al. | |
| 11,547,282 B2 | 1/2023 | Weise et al. | |
| 11,607,150 B2 | 3/2023 | Schweikert et al. | |
| 11,621,518 B2 | 4/2023 | Stats et al. | |
| 11,630,009 B2 * | 4/2023 | Misener | A61B 5/065 |
| | | | 600/413 |
| 11,707,205 B2 | 7/2023 | Messerly et al. | |
| 11,806,096 B2 | 11/2023 | Flatt et al. | |
| 11,850,073 B2 | 12/2023 | Wright et al. | |
| 11,931,112 B2 | 3/2024 | Thompson et al. | |
| 12,038,338 B2 * | 7/2024 | Misener | A61B 18/1492 |
| 12,048,478 B2 | 7/2024 | Tegg et al. | |
| 12,089,815 B2 | 9/2024 | Sowards et al. | |
| 2002/0019627 A1 | 2/2002 | Maguire et al. | |
| 2002/0087206 A1 | 7/2002 | Hirschberg et al. | |
| 2002/0166190 A1 | 11/2002 | Miyake et al. | |
| 2002/0188285 A1 | 12/2002 | Brown | |
| 2002/0198457 A1 | 12/2002 | Tearney et al. | |
| 2003/0045798 A1 | 3/2003 | Hular et al. | |
| 2003/0092995 A1 | 5/2003 | Thompson | |
| 2004/0039274 A1 | 2/2004 | Benaron et al. | |
| 2004/0111020 A1 | 6/2004 | Long | |
| 2004/0111147 A1 | 6/2004 | Rabkin et al. | |
| 2004/0242995 A1 | 12/2004 | Maschke | |
| 2004/0247268 A1 | 12/2004 | Ishihara et al. | |
| 2004/0260182 A1 | 12/2004 | Zuluaga et al. | |
| 2005/0033264 A1 | 2/2005 | Redinger | |
| 2005/0113719 A1 | 5/2005 | Saadat | |
| 2005/0272975 A1 | 12/2005 | McWeeney et al. | |
| 2006/0013523 A1 | 1/2006 | Childlers et al. | |
| 2006/0030753 A1 | 2/2006 | Boutillette et al. | |
| 2006/0036164 A1 | 2/2006 | Wilson et al. | |
| 2006/0069305 A1 | 3/2006 | Couvillon et al. | |
| 2006/0100610 A1 | 5/2006 | Wallace et al. | |
| 2006/0189959 A1 | 8/2006 | Schneiter | |
| 2006/0200049 A1 | 9/2006 | Leo et al. | |
| 2006/0241395 A1 | 10/2006 | Kruger et al. | |
| 2006/0241492 A1 | 10/2006 | Boese et al. | |
| 2007/0060847 A1 | 3/2007 | Leo et al. | |
| 2007/0156019 A1 | 7/2007 | Larkin et al. | |
| 2007/0179485 A1 | 8/2007 | Yeik et al. | |
| 2007/0201793 A1 | 8/2007 | Askins et al. | |
| 2007/0225563 A1 | 9/2007 | Ogino | |
| 2007/0253673 A1 | 11/2007 | Nielsen et al. | |
| 2007/0265503 A1 | 11/2007 | Schlesinger et al. | |
| 2007/0287886 A1 | 12/2007 | Saadat | |
| 2007/0299425 A1 | 12/2007 | Waner et al. | |
| 2008/0034519 A1 | 2/2008 | Fujiwara | |
| 2008/0172119 A1 | 7/2008 | Yamasaki et al. | |
| 2008/0183128 A1 | 7/2008 | Morriss et al. | |
| 2008/0281293 A1 | 11/2008 | Peh et al. | |
| 2008/0285909 A1 | 11/2008 | Younge et al. | |
| 2009/0005675 A1 | 1/2009 | Grunwald et al. | |
| 2009/0018393 A1 | 1/2009 | Dick et al. | |
| 2009/0046980 A1 | 2/2009 | Rohlen | |
| 2009/0062634 A1 | 3/2009 | Say et al. | |
| 2009/0137952 A1 | 5/2009 | Ramamurthy et al. | |
| 2009/0208143 A1 | 8/2009 | Yoon et al. | |
| 2009/0227992 A1 | 9/2009 | Nir et al. | |
| 2009/0234328 A1 | 9/2009 | Cox et al. | |
| 2009/0253967 A1 | 10/2009 | Gill et al. | |
| 2009/0270729 A1 | 10/2009 | Corbucci et al. | |
| 2009/0304582 A1 | 12/2009 | Rousso et al. | |
| 2009/0318757 A1 | 12/2009 | Singh | |
| 2009/0324161 A1 | 12/2009 | Prisco | |
| 2010/0016729 A1 | 1/2010 | Futrell | |
| 2010/0030063 A1 | 2/2010 | Lee et al. | |
| 2010/0063534 A1 | 3/2010 | Kugler et al. | |
| 2010/0114115 A1 | 5/2010 | Schlesinger et al. | |
| 2010/0114190 A1 | 5/2010 | Bendett et al. | |
| 2010/0139669 A1 | 6/2010 | Piferi et al. | |
| 2010/0204569 A1 | 8/2010 | Burnside et al. | |
| 2010/0286531 A1 | 11/2010 | Ryan et al. | |
| 2010/0292758 A1 | 11/2010 | Lee et al. | |
| 2011/0087112 A1 | 4/2011 | Leo et al. | |
| 2011/0098533 A1 | 4/2011 | Onoda et al. | |
| 2011/0144481 A1 | 6/2011 | Feer et al. | |
| 2011/0144630 A1 | 6/2011 | Loeb | |
| 2011/0166442 A1 | 7/2011 | Sarvazyan | |
| 2011/0172680 A1 | 7/2011 | Younge et al. | |
| 2011/0178509 A1 | 7/2011 | Zerfas et al. | |
| 2011/0196248 A1 | 8/2011 | Grunwald | |
| 2011/0245662 A1 | 10/2011 | Eggers et al. | |
| 2011/0295108 A1 | 12/2011 | Cox et al. | |
| 2012/0046562 A1 | 2/2012 | Powers et al. | |
| 2012/0116161 A1 | 5/2012 | Nieman et al. | |
| 2012/0143029 A1 | 6/2012 | Silverstein et al. | |
| 2012/0184827 A1 | 7/2012 | Shwartz et al. | |
| 2012/0184955 A1 | 7/2012 | Pivotto et al. | |
| 2012/0321243 A1 | 12/2012 | Younge et al. | |
| 2013/0096482 A1 | 4/2013 | Bertrand et al. | |
| 2013/0104884 A1 | 5/2013 | Vazales et al. | |
| 2013/0150732 A1 | 6/2013 | Manzke et al. | |
| 2013/0188855 A1 | 7/2013 | Desjardins et al. | |
| 2013/0190741 A1 | 7/2013 | Moll et al. | |
| 2013/0204124 A1 | 8/2013 | Duindam et al. | |
| 2013/0211246 A1 | 8/2013 | Parasher | |
| 2013/0296652 A1 | 11/2013 | Farr | |
| 2013/0296693 A1 | 11/2013 | Wenzel et al. | |
| 2013/0310668 A1 | 11/2013 | Young | |
| 2013/0324840 A1 | 12/2013 | Zhongping et al. | |
| 2014/0031674 A1 | 1/2014 | Newman et al. | |
| 2014/0046261 A1 | 2/2014 | Newman et al. | |
| 2014/0058368 A1 | 2/2014 | Hogue | |
| 2014/0073950 A1 | 3/2014 | Akui et al. | |
| 2014/0088413 A1 | 3/2014 | Von Buesh et al. | |
| 2014/0121468 A1 | 5/2014 | Eichenholz | |
| 2014/0155948 A1 | 6/2014 | Walsh et al. | |
| 2014/0180087 A1 | 6/2014 | Millett et al. | |
| 2014/0188133 A1 | 7/2014 | Misener | |
| 2014/0221829 A1 | 8/2014 | Maitland et al. | |
| 2014/0259477 A1 | 9/2014 | Huang | |
| 2014/0268167 A1 | 9/2014 | Friedman et al. | |
| 2014/0275997 A1 | 9/2014 | Chopra et al. | |
| 2014/0318825 A1 | 10/2014 | Erb et al. | |
| 2014/0323887 A1 | 10/2014 | Anderson et al. | |
| 2014/0378945 A1 | 12/2014 | Beri | |
| 2015/0029511 A1 | 1/2015 | Hooft et al. | |
| 2015/0031987 A1 | 1/2015 | Pameijer et al. | |
| 2015/0045649 A1 | 2/2015 | O'Dea et al. | |
| 2015/0080688 A1 | 3/2015 | Cinbis et al. | |
| 2015/0099979 A1 | 4/2015 | Caves et al. | |
| 2015/0105654 A1 | 4/2015 | Meyer | |
| 2015/0119700 A1 * | 4/2015 | Liang | A61B 6/12 |
| | | | 600/424 |
| 2015/0119724 A1 | 4/2015 | Weber et al. | |
| 2015/0209113 A1 | 7/2015 | Burkholz et al. | |
| 2015/0209117 A1 | 7/2015 | Flexman et al. | |
| 2015/0244465 A1 | 8/2015 | Chou et al. | |
| 2015/0270900 A1 | 9/2015 | Hilario et al. | |
| 2015/0272445 A1 | 10/2015 | Rozental et al. | |
| 2015/0301288 A1 | 10/2015 | Thornton, Jr. | |
| 2015/0305816 A1 | 10/2015 | Hadzic | |
| 2015/0320977 A1 | 11/2015 | Vitullo et al. | |
| 2016/0018602 A1 | 1/2016 | Govari et al. | |
| 2016/0151115 A1 | 6/2016 | Karguth et al. | |
| 2016/0166326 A1 | 6/2016 | Bakker et al. | |
| 2016/0166341 A1 | 6/2016 | Iordachita et al. | |
| 2016/0184020 A1 | 6/2016 | Kowalewski et al. | |
| 2016/0256228 A1 | 9/2016 | Haartsen et al. | |
| 2016/0262627 A1 | 9/2016 | Hecker et al. | |

(56) References Cited

U.S. PATENT DOCUMENTS

| | | |
|---|---|---|
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2016/0374589 A1 | 12/2016 | Misener et al. |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1 | 3/2017 | Silverstein et al. |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0290542 A1 | 10/2017 | Chandrasoma |
| 2017/0296037 A1 | 10/2017 | Yoshino |
| 2017/0303824 A1 | 10/2017 | Schlesinger et al. |
| 2017/0311924 A1 | 11/2017 | Sudol |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0093078 A1 | 4/2018 | Patil et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1* | 10/2018 | Messerly ............ A61B 5/0084 |
| 2018/0317751 A1 | 11/2018 | Kuboi et al. |
| 2018/0339134 A1 | 11/2018 | Leo |
| 2018/0360545 A1 | 12/2018 | Cole et al. |
| 2018/0369432 A1 | 12/2018 | Zaborsky |
| 2019/0008376 A1 | 1/2019 | Wortelboer et al. |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0192818 A1 | 6/2019 | Koda et al. |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1 | 12/2019 | Courtney et al. |
| 2020/0022587 A1 | 1/2020 | Glover et al. |
| 2020/0046434 A1 | 2/2020 | Graetzel et al. |
| 2020/0060718 A1 | 2/2020 | Patel et al. |
| 2020/0069192 A1 | 3/2020 | Sanborn et al. |
| 2020/0093353 A1 | 3/2020 | Tezuka et al. |
| 2020/0155073 A1 | 5/2020 | Hwang et al. |
| 2020/0170724 A1 | 6/2020 | Flatt et al. |
| 2020/0188036 A1 | 6/2020 | Ding et al. |
| 2020/0238051 A1 | 7/2020 | Hwang et al. |
| 2020/0261720 A1 | 8/2020 | Danitz et al. |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1* | 2/2021 | Thompson ........ A61M 25/0097 |
| 2021/0113274 A1 | 4/2021 | Bydlon et al. |
| 2021/0154440 A1 | 5/2021 | Misener |
| 2021/0156676 A1 | 5/2021 | Messerly et al. |
| 2021/0205585 A1 | 7/2021 | Ullmann et al. |

| | | |
|---|---|---|
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1 | 9/2021 | Tegg et al. |
| 2021/0290315 A1 | 9/2021 | Lampert et al. |
| 2021/0298680 A1 | 9/2021 | Sowards et al. |
| 2021/0299879 A1 | 9/2021 | Pinter et al. |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0039632 A1 | 2/2022 | Polejaev et al. |
| 2022/0039744 A1 | 2/2022 | Koenig |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2022/0361762 A1 | 11/2022 | Lalancette et al. |
| 2023/0082991 A1 | 3/2023 | Sowards et al. |
| 2023/0149080 A1 | 5/2023 | Wong et al. |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1 | 11/2023 | Moore |
| 2023/0414293 A1 | 12/2023 | Farley et al. |
| 2023/0417998 A1 | 12/2023 | Misener et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |
| 2024/0423456 A1 | 12/2024 | Sowards et al. |
| 2025/0176853 A1 | 6/2025 | Sowards et al. |
| 2025/0186134 A1 | 6/2025 | Sowards et al. |
| 2025/0249208 A1 | 8/2025 | Sowards et al. |
| 2025/0288366 A1 | 9/2025 | Misener et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 2809249 B1 | 12/2018 |
| EP | 3545849 A1 | 10/2019 |
| EP | 3725252 A1 | 10/2020 |
| WO | 99/64099 A1 | 12/1999 |
| WO | 2006080076 A1 | 8/2006 |
| WO | 2006122001 A2 | 11/2006 |
| WO | 2009/155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016/061431 A1 | 4/2016 |
| WO | 2016193051 A1 | 12/2016 |
| WO | 2018071490 A1 | 4/2018 |
| WO | 2018/096491 A1 | 5/2018 |
| WO | 2019037071 A1 | 2/2019 |
| WO | 2019/046769 A1 | 3/2019 |
| WO | 2019230713 A1 | 12/2019 |
| WO | 2020/142470 A1 | 7/2020 |
| WO | 2021021408 A1 | 2/2021 |
| WO | 2021030092 A1 | 2/2021 |

(56) References Cited

FOREIGN PATENT DOCUMENTS

| WO | 2021108688 A1 | 6/2021 |
|---|---|---|
| WO | 2021108697 A1 | 6/2021 |
| WO | 2021144317 A1 | 7/2021 |
| WO | 2021178578 A1 | 9/2021 |
| WO | 2022/031613 A1 | 2/2022 |
| WO | 2022/081586 A1 | 4/2022 |
| WO | 2022/081723 A1 | 4/2022 |
| WO | 2022109045 A1 | 5/2022 |
| WO | 2022115624 A1 | 6/2022 |
| WO | 2022221608 A1 | 10/2022 |
| WO | 2023043947 A1 | 3/2023 |
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

PCT/US2023/019130 filed Apr. 19, 2023 International Search Report and Written Opinion dated Jul. 19, 2023.
PCT/US2023/020042 filed Apr. 26, 2023 International Search Report and Written Opinion dated Sep. 26, 2023.
PCT/US2023/020044 filed Apr. 26, 2023 International Search Report and Written Opinion dated Jul. 19, 2023.
PCT/US2023/025757 filed Jun. 20, 2023 International Search Report and Written Opinion dated Sep. 11, 2023.
PCT/US2023/027527 filed Jul. 12, 2023 International Search Report and Written Opinion dated Oct. 16, 2023.
U.S. Appl. No. 17/187,536, filed Feb. 26, 2021 Final Office Action dated Sep. 20, 2023.
U.S. Appl. No. 17/217,852, filed Mar. 30, 2021 Ex Parte Quayle Action dated Sep. 8, 2023.
U.S. Appl. No. 17/499,644, filed Oct. 12, 2021 Notice of Allowance dated Sep. 18, 2023.
U.S. Appl. No. 17/697,895, filed Mar. 17, 2022 Advisory Action dated Sep. 8, 2023.
U.S. Appl. No. 17/697,895, filed Mar. 17, 2022 Final Office Action dated Aug. 16, 2023.
U.S. Appl. No. 17/217,852, filed Mar. 30, 2021 Restriction Requirement dated Mar. 21, 2023.
U.S. Appl. No. 17/967,794, filed Oct. 17, 2022 Notice of Allowance dated Feb. 15, 2023.
PCT/US2023/014849 filed Mar. 8, 2023 International Search Report and Written Opinion dated Jun. 7, 2023.
PCT/US2023/015416 filed Mar. 16, 2023 International Search Report and Written Opinion dated May 26, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
U.S. Appl. No. 17/187,536, filed Feb. 26, 2021 Non-Final Office Action dated May 17, 2023.
U.S. Appl. No. 17/217,852, filed Mar. 30, 2021 Non Final Office Action dated Jun. 7, 2023.
U.S. Appl. No. 17/499,644, filed Oct. 12, 2021 Restriction Requirement dated Jul. 11, 2023.
U.S. Appl. No. 17/697,895, filed Mar. 17, 2022 Non Final Office Action dated Jun. 14, 2023.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).

PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/535,406, filed Nov. 24, 2021 Non-Final Office Action dated Feb. 15, 2024.
U.S. Appl. No. 17/689,773, filed Mar. 8, 2022 Non-Final Office Action dated Mar. 19, 2024.
U.S. Appl. No. 17/731,155, filed Apr. 27, 2022 Restriction Requirement dated Feb. 28, 2024.
U.S. Appl. No. 17/849,447, filed Jun. 24, 2022 Non-Final Office Action dated Apr. 10, 2024.
PCT/US2021 /059755 filed Nov. 17, 2021 International Search Report and Written Opinion dated Apr. 29, 2022.
PCT/US2021/019713 filed Feb. 25, 2021 International Search Report and Written Opinion dated Jul. 6, 2021.
PCT/US2021/020079 filed Feb. 26, 2021 International Search Report and Written Opinion dated Jun. 4, 2021.
PCT/US2021/020732 filed Mar. 3, 2021 International Search Report and Written Opinion dated Jul. 5, 2021.
PCT/US2021/024969 filed Mar. 30, 2021 International Search Report and Written Opinion dated Jul. 19, 2021.
PCT/US2021/060849 filed Nov. 24, 2021 International Search Report and Written Opinion dated Mar. 9, 2022.
U.S. Appl. No. 17/185,777, filed Feb. 25, 2021 Notice of Allowance dated Jun. 10, 2022.
U.S. Appl. No. 17/187,536, filed Feb. 26, 2021 Advisory Action dated Nov. 21, 2023.
U.S. Appl. No. 17/187,536, filed Feb. 26, 2021 Non-Final Office Action dated Dec. 15, 2023.
U.S. Appl. No. 17/217,852, filed Mar. 30, 2021 Notice of Allowance dated Nov. 7, 2023.
U.S. Appl. No. 17/535,406, filed Nov. 24, 2021 Restriction Requirement dated Nov. 24, 2023.
U.S. Appl. No. 17/697,895, filed Mar. 17, 2022 Non-Final Office Action dated Jan. 11, 2024.
PCT/US2021/054596 filed Oct. 12, 2021 International Search Report and Written Opinion dated Jan. 26, 2022.
PCT/US2022/043698 filed Sep. 15, 2022 International Search Report and Written Opinion dated Dec. 19. 2022.
U.S. Appl. No. 17/187,536, filed Feb. 26, 2021 Final Office Action dated Jul. 2, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/696,675, filed Mar. 16, 2022 Non-Final Office Action dated Jun. 11, 2024.
U.S. Appl. No. 17/697,895, filed Mar. 17, 2022 Notice of Allowance dated May 8, 2024.
U.S. Appl. No. 17/725,394, filed Apr. 20, 2022 Non-Final Office Action dated Jun. 17, 2024.
U.S. Appl. No. 18/524,620, filed Nov. 30, 2023 Non-Final Office Action dated Jun. 18, 2024.
PCT/US2023/015536 filed Mar. 17, 2023 International Preliminary Report on Patentability dated Sep. 10, 2024.
PCT/US2023/018076 filed Apr. 10, 2023 International Preliminary Report on Patentability dated Oct. 8, 2024.
U.S. Appl. No. 17/187,536, filed Feb. 26, 2021 Advisory Action dated Oct. 9, 2024.
U.S. Appl. No. 17/187,536, filed Feb. 26, 2021 Notice of Allowance dated Oct. 29, 2024.
U.S. Appl. No. 17/191,551, filed Mar. 3, 2021 Non-Final Office Action dated Aug. 16, 2024.
U.S. Appl. No. 17/529,022, filed Nov. 17, 2021 Non-Final Office Action dated Sep. 30, 2024.
U.S. Appl. No. 17/535,406, filed Nov. 24, 2021 Notice of Allowance dated Oct. 23, 2024.
U.S. Appl. No. 17/731,155, filed Apr. 27, 2022 Non-Final Office Action dated Aug. 22, 2024.
U.S. Appl. No. 17/849,447, filed Jun. 24, 2022 Advisory Action dated Oct. 24, 2024.

(56) References Cited

OTHER PUBLICATIONS

U.S. Appl. No. 17/849,447, filed Jun. 24, 2022 Final Office Action dated Aug. 8, 2024.

U.S. Appl. No. 18/141,289, filed Apr. 28, 2023 Non-Final Office Action dated Sep. 28, 2024.

U.S. Appl. No. 18/524,620, filed Nov. 30, 2023 Notice of Allowance dated Sep. 12, 2024.

PCT/US2023/019130 filed Apr. 19, 2023 International Preliminary Report on Patentability dated Oct. 8, 2024.

PCT/US2023/020044 filed Apr. 26, 2023 International Preliminary Report on Patentability dated Oct. 29, 2024.

U.S. Appl. No. 17/191,551, filed Mar. 3, 2021 Notice of Allowance dated Nov. 8, 2024.

U.S. Appl. No. 17/529,022, filed Nov. 17, 2021 Notice of Allowance dated Jan. 2, 2025.

U.S. Appl. No. 17/529,022, filed Nov. 17, 2021 Restriction Requirement dated May 2, 2024.

U.S. Appl. No. 17/689,773, filed Mar. 8, 2022 Advisory Action dated Nov. 1, 2024.

U.S. Appl. No. 17/689,773, filed Mar. 8, 2022 Notice of Allowance dated Jan. 15, 2025.

U.S. Appl. No. 17/696,675, filed Mar. 16, 2022 Advisory Action dated Feb. 6, 2025.

U.S. Appl. No. 17/696,675, filed Mar. 16, 2022 Final Office Action dated Dec. 5, 2024.

U.S. Appl. No. 17/717,919, filed Apr. 11, 2022 Restriction Requirement dated Apr. 23, 2025.

U.S. Appl. No. 17/725,394, filed Apr. 20, 2022 Final Office Action dated Mar. 27, 2025.

U.S. Appl. No. 17/725,394, filed Apr. 20, 2022 Non-Final Office Action dated Nov. 19, 2024.

U.S. Appl. No. 17/731,129, filed Apr. 27, 2022 Non-Final Office Action dated Apr. 28, 2025.

U.S. Appl. No. 17/731,129, filed Apr. 27, 2022 Restriction Requirement dated Feb. 28, 2025.

U.S. Appl. No. 17/731,155, filed Apr. 27, 2022 Advisory Action dated Apr. 3, 2025.

U.S. Appl. No. 17/731,155, filed Apr. 27, 2022 Final Office Action dated Jan. 24, 2025.

U.S. Appl. No. 17/849,447, filed Jun. 24, 2022 Non-Final Office Action dated Jan. 17, 2025.

U.S. Appl. No. 17/849,447, filed Jun. 24, 2022 Restriction Requirement dated Apr. 15, 2024.

U.S. Appl. No. 17/945,875, filed Sep. 15, 2022 Non-Final Office Action dated Feb. 27, 2025.

U.S. Appl. No. 18/075,280, filed Dec. 5, 2022 Restriction Requirement dated Mar. 28, 2025.

U.S. Appl. No. 18/141,289, filed Apr. 28, 2023 Notice of Allowance dated Jan. 10, 2025.

U.S. Appl. No. 18/607,165, filed Mar. 15, 2024 Non-Final Office Action dated Jan. 15, 2025.

U.S. Appl. No. 18/607,165, filed Mar. 15, 2024 Notice of Allowance dated Apr. 3, 2025.

U.S. Appl. No. 17/696,675, filed Mar. 16, 2022 Notice of Allowance dated Jun. 17, 2025.

U.S. Appl. No. 17/717,919, filed Apr. 11, 2022 Non-Final Office Action dated Jul. 1, 2025.

U.S. Appl. No. 17/721,333, filed Apr. 14, 2022 Restriction Requirement dated May 6, 2025.

U.S. Appl. No. 17/725,394, filed Apr. 20, 2022 Advisory Action dated Jun. 5, 2025.

U.S. Appl. No. 17/725,394, filed Apr. 20, 2022 Non-Final Office Action dated Jun. 25, 2025.

U.S. Appl. No. 17/731,155, filed Apr. 27, 2022 Non-Final Office Action dated Jul. 15, 2025.

U.S. Appl. No. 17/849,447, filed Jun. 24, 2022 Final Office Action dated May 7, 2025.

U.S. Appl. No. 17/945,875, filed Sep. 15, 2022 Notice of Allowance dated Jul. 21, 2025.

U.S. Appl. No. 18/075,280, filed Dec. 5, 2022 Non-Final Office Action dated Jun. 11, 2025.

U.S. Appl. No. 17/721,333, filed Apr. 14, 2022 Non-Final Office Action dated Oct. 16, 2025.

U.S. Appl. No. 17/731,129, filed Apr. 27, 2022 Advisory Action dated Oct. 30, 2025.

U.S. Appl. No. 17/731,129, filed Apr. 27, 2022 Final Office Action dated Aug. 27, 2025.

U.S. Appl. No. 17/849,447, filed Jun. 24, 2022 Ex Parte Quayle Action dated Sep. 4, 2025.

* cited by examiner

PROXIMAL

DISTAL

PROXIMAL

DISTAL

ECCENTRIC SINGLE-CORE FIBER-OPTIC ENABLED MEDICAL DEVICE

BACKGROUND

Elongate medical devices configured for insertion within a patient vasculature may be utilized to perform a myriad of treatments and diagnoses. Fiber optic enabled vascular devices can be beneficial in the providing the vascular treatments. Fiber optic shape sensing capability can also enable proper placement of the vascular devices. Shapes sensing optical fibers typically utilize multi-core optical fibers. However, multi-core optical fibers result in elevated costs of the medical devices and the related systems. Furthermore, the added complexity of the multi-core optical fibers can negative affect reliability resulting in increased risk to the patient and further increased cost to the healthcare provider.

Disclosed herein are medical systems and methods that address the forgoing.

SUMMARY

Briefly summarized, disclosed herein is a medical system. According to some embodiments, the medical system includes an elongate medical device configured for insertion within a blood vessel of a patient, where the medical device includes an optical fiber extending along a longitudinal length the medical device to a distal end of the medical device. The optical fiber has a single core fiber extending along the optical fiber, where the single core fiber is disposed radially offset from a central axis of the optical fiber. The single core fiber includes a plurality of sensors distributed along the longitudinal length, where each sensor is configured to (i) reflect a light signal of a different spectral width based on received incident light, and (ii) change a characteristic of the reflected light signal based on a state of the optical fiber.

The system further includes a console operatively coupled with the optical fiber. The console includes a light source, an optical receiver, one or more processors, and a non-transitory computer-readable medium having stored thereon logic that, when executed by the one or more processors, causes operations of the system that include (i) projecting a light distally along the optical fiber, (ii) receiving at least one reflected light signal from the optical fiber, (iii) determining a state of the optical fiber, based on the at least one reflected light signal, and (iv) communicating the state to a user.

In some embodiments of the system, the state of the optical fiber includes a fluctuating movement of at least a distal portion of the optical fiber, and the operations further include (i) extracting from the at least one reflected light signal present fluctuating movement data, (ii) comparing the present fluctuating movement data with one or more fluctuating movement limits stored in the non-transitory computer-readable medium, where the fluctuating movement limits pertain to movement of the distal portion in response to oscillating anatomic motion adjacent a cavoatrial junction of the patient, and (iii) determining, as result of the comparison, that the distal end of the medical device is disposed adjacent the cavoatrial junction the blood vessel.

In some embodiments of the system, the state of the optical fiber further includes a condition experienced by an inserted portion of the optical fiber, and the operations further include (i) receiving one or more reflected light signals from a subset of the plurality of sensors, the subset disposed along the inserted portion, (ii) extracting present condition data from the one or more reflected light signals, and (iii) determining a length of the inserted portion based on the present condition data.

In some embodiments of the system, the state of the optical fiber includes a compressive strain of the optical fiber caused by a contact force applied to the distal end during advancement of the medical device along the blood vessel, and the operations further include (i) extracting from the at least one reflected light signal present compressive strain data, and (ii) identifying from the compressive strain data check valves disposed along the blood vessel.

In some embodiments of the system, the state of the optical fiber includes a compressive strain of the optical fiber caused by a contact force applied to the distal end of the optical fiber, and the operations further include (i) extracting from the at least one reflected light signal present compressive strain data, (ii) comparing the present compressive strain data with a compressive strain safety limit stored in the non-transitory computer-readable medium, the compressive strain safety limit defining a safe limit for contact of the distal end with the anatomical elements, and (iii) providing an alert to the user when the present compressive strain data exceeds the compressive strain safety limit.

In some embodiments of the system, the state of the optical fiber includes a temperature experienced by one or more of the plurality of sensors when the optical fiber is inserted within the patient, and the operations further include (i) receiving one or more reflected light signals from the one or more sensors, (ii) extracting present temperature data from the one or more reflected light signals, and (iii) determining a core temperature of the patient from the present temperature data.

In some embodiments of the system, the optical fiber extends along a catheter inserted within the blood vessel, where the catheter is configured to deliver an infusate to the blood vessel, and the state of the optical fiber includes a first temperature experienced by a section of the optical fiber extending beyond a distal end of the catheter during non-delivery of the infusate and a second temperature experienced by the section during delivery of the infusate. In such embodiments, the operations further include (i) receiving a first reflected light signal from a sensor disposed along the section during non-delivery of the infusate, the first reflected light signal based on the first temperature, (ii) receiving a second reflected light signal from the sensor, the second reflected light signal based on the second temperature, (iii) extracting from the first and second reflected light signals present temperature difference data between the first and second temperatures, (iv) comparing the present temperature difference data with a temperature difference limit stored in the non-transitory computer-readable medium. The operations further include determining, as result of the comparison, (i) when the infusate is delivered and (ii) when the infusate is not delivered.

In some embodiments of the system, the infusate is a flushing solution for the catheter, where initiating and terminating the delivery of the infusate defines a flushing event. In such embodiments, the operations further include determining at least one of a frequency or a number of flushing events.

In some embodiments of the system, the delivery rate of the infusate is known such that initiating and terminating the delivery of the infusate defines an infused volume of the infusate, and the operations further include determining of the infused volume.

In some embodiments of the system, the state of the optical fiber includes a damage to the optical fiber, and the operations further include determining the damage of the optical fiber, where determining the damage includes at least one of (i) receiving a subset of reflected light signals from a respective subset of sensors, the subset of reflected light signals having a spectral width that exceeds a defined spectral-width range stored in the non-transitory computer-readable medium, or (ii) not receiving a reflected light signal from at least one sensor.

In some embodiments of the system, the operations further include (i) determining a longitudinal location of the respective subset of sensors or the at least one sensor along the along the optical fiber and (ii) relating the longitudinal location of the respective subset of sensors or the at least one sensor with a longitudinal location of the damage along the optical fiber.

In some embodiments of the system, the operations further include (i) propagating an illuminating light distally along the optical fiber, (ii) projecting the illuminating light distally away from a distal of the optical fiber, (iii) receiving an image light signal via the distal end, (iv) propagating the image light signal proximally along the optical fiber, (v) extracting image data from the image light signal, and (vi) portraying the image data in the form of an image on a display of the system.

In some embodiments of the system, the optical fiber is inserted within the blood vessel, and the operations further include (i) projecting a light defining a first wavelength distally away from a distal end of the optical fiber into blood of the blood vessel, (ii) receiving a reflected light signal having a second wavelength via the distal end, (iii) extracting from the reflected light signal a present wavelength shift between the first wavelength and the second wavelength, (iv) comparing the present wavelength shift with one or more wavelength shift limits stored in the non-transitory computer-readable medium, and (v) determining, as result of the comparison, at least one of a direction of blood flow or a velocity of the blood flow.

In some embodiments of the system, the operations further include (i) projecting the light toward a coating of the medical device, where the coating is configured to define a light characteristic based on a pH of a fluid in contact with the medical device, (ii) receiving a light signal from the coating in response to the projected light, where the light signal includes the light characteristic, (iii) extracting the pH from the light signal, and (iv) communicating the pH to the user.

In some embodiments of the system, the operations further include (i) projecting the light into blood of the patient, (ii) receiving a light signal from the blood in response to the projected light, where the light signal includes a light characteristic based on a blood oxygen level, (iii) extracting the blood oxygen level from the light signal, and (iv) communicating the blood oxygen level to the user.

In some embodiments of the system, the elongate medical device includes a catheter, a stylet, a probe, or a guidewire.

Also disclosed herein is an elongate medical device to be inserted within a patient body, that according to some embodiments, includes an optical fiber extending between an optical interface at a proximal end of the medical device and a distal end of the medical device, where the optical fiber includes a single core fiber extending along a longitudinal length of the optical fiber. In such embodiments, the single core fiber is disposed radially offset from a central axis of the optical fiber, and the single core fiber is configured to receive an incident light via the optical interface and a propagate the incident light distally along the longitudinal length. The single core fiber includes a plurality of sensors distributed along the longitudinal length, where each sensor of the plurality of sensors is configured to (i) reflect a light signal of a different spectral width based on the incident light, and (ii) change a characteristic of the reflected light signal based on a state of the single core fiber, and where the state of the single core fiber is defined by a condition of the patient body.

Also disclosed herein is a method performed by a medical system, that according to some embodiments, includes projecting a light distally along an optical fiber of the system, the optical fiber disposed within a patient body, where the optical fiber includes a single core fiber disposed radially offset from a central axis of the optical fiber. The single core fiber is configured to (i) receive the light via an optical interface of the optical fiber coupled with a console of system and (ii) propagate the light distally along a longitudinal length of the single core fiber. The method further includes (i) receiving a light signal from the optical fiber, the light signal propagating proximally along the single core fiber, (ii) extracting from the light signal a number of conditions experienced by the single core fiber; and (iii) communicating the number of conditions to a user.

In some embodiments of the method, the number of conditions experienced by the single core fiber includes a damage to the single core fiber.

In some embodiments of the method, the number of conditions experienced by the single core fiber includes conditions of the patient body that include one or more of a flow velocity of a blood, a flow direction of the blood, a pH of the blood, or an oxygen level of the blood.

In some embodiments of the method, the single core fiber includes a plurality of sensors distributed along the longitudinal length, each sensor of the plurality of sensors configured to (i) define a reflected light signal of a different spectral width based on the light, and (ii) change a characteristic of the reflected light signal based on the number of conditions experienced by the single core fiber, and the number of conditions experienced by the single core fiber include one or more of (i) a core temperature of the patient body, (ii) a shape of the single core fiber defined by a shape of a blood vessel, (iii) a fluctuating motion of the single core fiber consistent with placement of a distal end the optical fiber adjacent a cavoatrial junction, or (iv) a compressive force applied longitudinally to the optical fiber resulting from contact of the distal end of the optical fiber with an anatomical element of the patient body.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Figure 1:
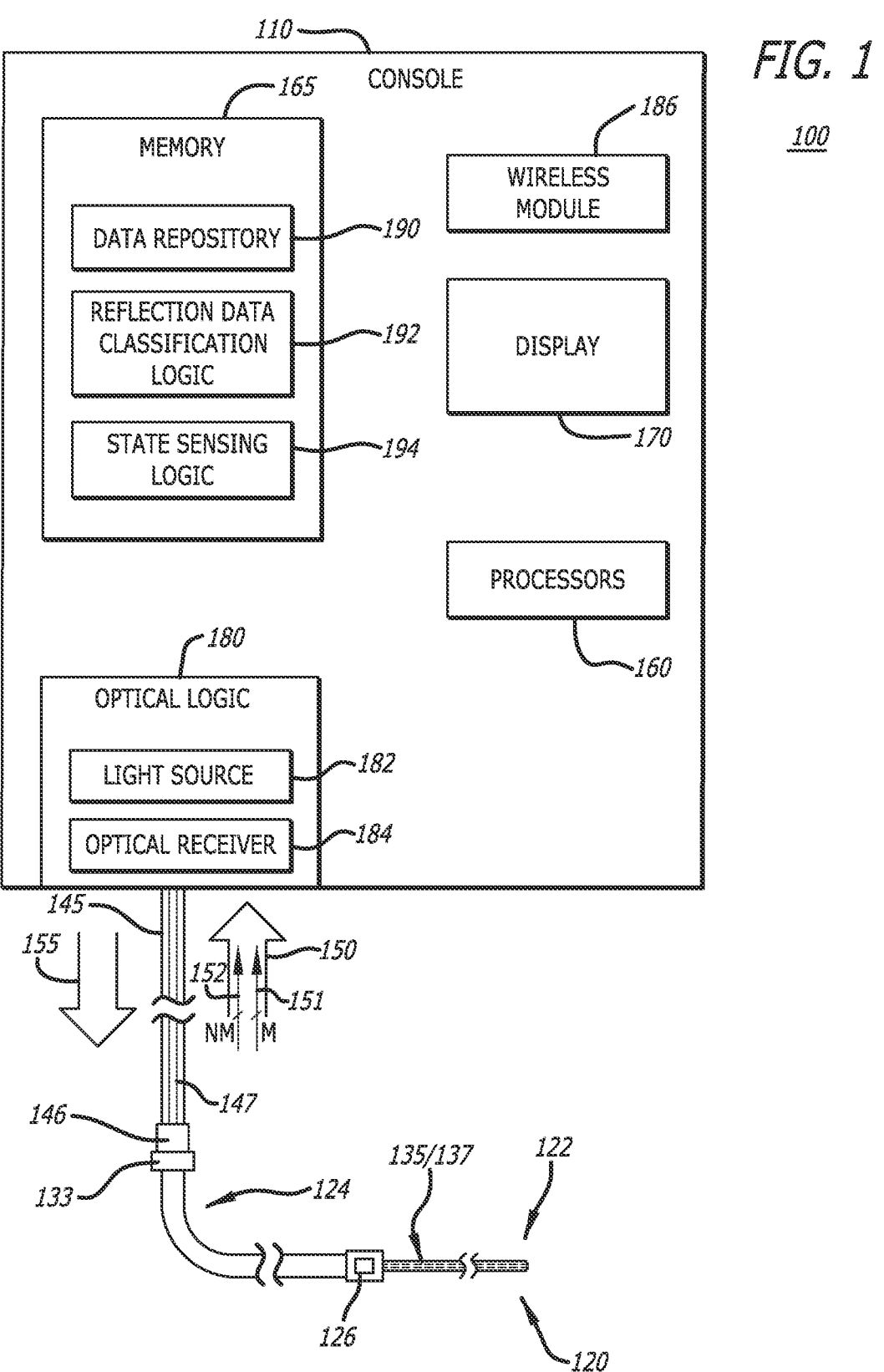
FIG. 1 is an illustrative embodiment of a medical system including an elongate medical device having an optical fiber, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including an optical fiber disclosed herein. As used herein, the proximal portion of an optical fiber is the portion nearest a practitioner during use or least inserted within a patient, while the distal portion is the portion at the opposite end. For example, the proximal end of the optical fiber is defined as the end closest to the practitioner during utilization of the optical fiber. The distal end is the end opposite the proximal end, along the longitudinal direction of the optical fiber, e.g., the end furthest inserted into the patient.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit (ASIC), etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random-access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the logic may be stored in persistent storage.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations may be made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

FIG. 1 illustrates an embodiment of a medical system including a medical device. As shown, the medical system (system) 100 generally includes a console 110 and an elongate medical device (device) 120 communicatively coupled with the console 110. The device 120 defines a distal end 122 and includes a console connector 133 at a proximal end 124. The device 120 includes an optical fiber 135 including multiple core fibers extending along a length of the device 120 as further described below. The console connector 133 enables the device 120 to be operably connected to the console 110 via an interconnect 145 including one or more optical fibers 147 (hereinafter, "optical fiber(s)"). Herein, the connector 146 is configured to engage (mate) with the console connector 133 to allow for the propagation of light between the console 110.

The device 120 may be configured to perform any of a variety of medical procedures. As such, the device 120 may be a component of or employed with a variety of medical instruments/devices 119. In some implementations, the device 120 may take the form of a guidewire, a stylet, or a catheter, for example. The device 120 may be formed of a metal, a plastic or a combination thereof. In some embodiments, the device 120 may include a lumen extending therealong having an optical fiber 135 disposed therein.

In some implementations, the device 120 may be integrated into a vascular catheter. Other exemplary implementations include drainage catheters, surgery devices, stent insertion and/or removal devices, biopsy devices, endoscopes, and kidney stone removal devices. In short, the device 120 may be employed with, or the device 120 may be a component of, any medical device 119 that is inserted into a patient.

According to one embodiment, the console 110 includes one or more processors 160, a memory 165, a display 170, and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Publication No. 2019/0237902, the entire contents of which are incorporated by reference herein. The one or more processors 160, with access to the memory 165 (e.g., non-volatile memory or non-transitory, computer-readable medium), are included to control functionality of the console 110 during operation. As shown, the display 170 may be a liquid crystal diode (LCD) display integrated into the console 110 and employed as a user interface to display information to the clinician, especially during an instrument placement procedure. In another embodiment, the display 170 may be separate from the console 110. Although not shown, a user interface is configured to provide user control of the console 110.

Referring still to FIG. 1, the optical logic 180 is configured to support operability of the device 120 and enable the return of information to the console 110, which may be used to determine the physical state associated with the device 120 along or an image of the patient body. The physical state of the device 120 may be based on changes in characteristics of the reflected light signals 150 received at the console 110 from the device 120. The characteristics may include shifts in wavelength caused by strain on certain regions of the core fibers integrated within the optical fiber 135 positioned within or operating as the device 120, as shown below. As discussed herein, the optical fiber 135 may be comprised of a number (e.g., 1, 2, 3, 4, or more) of core fibers $137_1$-$137_M$ (M=1 for a single core, and M>2 for a multi-core), where the core fibers $137_1$-$137_M$ may collectively be referred to as core fiber(s) 137. Unless otherwise specified or the instant embodiment requires an alternative interpretation, embodiments discussed herein will refer to an optical fiber 135. From information associated with the reflected light signals 150, the console 110 may determine (through computation or extrapolation of the wavelength shifts) the physical state of the device 120 and/or physical conditions experienced by the probe 120, such as strain, temperature, pressure, or movement, for example.

According to one embodiment of the disclosure, as shown in FIG. 1, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the optical fiber 135 within the device 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the optical fiber 135 deployed within the device 120, and (ii) translate the reflected light signals 150 into reflection data (from a data repository 190), namely data in the form of electrical signals representative of the reflected light signals including wavelength shifts caused by strain. The reflected light signals 150 associated with different spectral widths may include reflected light signals 151 provided from sensors positioned in the center core fiber (reference) of the optical fiber 135 and/or reflected light signals 152 provided from sensors positioned in the periphery core fibers of the optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the one or more processors 160, which governs their operation. Also, the optical receiver 184 is operably coupled so as to provide the reflection data (from the data repository 190) to the memory 165 for storage and processing by reflection data classification logic 192. The reflection data classification logic 192 may be configured to: (i) identify which core fibers pertain to which of the received reflection data (from the data repository 190) and (ii) segregate the reflection data stored within the data repository 190 provided from reflected light signals 150 pertaining to similar regions of the device 120 or spectral widths into analysis groups. The reflection data for each analysis group is made available to state sensing logic 194 for analytics.

According to one embodiment of the disclosure, the state sensing logic 194 is configured to compare wavelength shifts measured by sensors deployed in each periphery core fiber at the same measurement region of the device 120 (or same spectral width) to the wavelength shift at a center core fiber of the optical fiber 135 positioned along central axis and operating as a neutral axis of bending. From these analytics, the state sensing logic 194 may determine the shape the core fibers have taken in three-dimensional space and may further determine the current physical state of the device 120 in three-dimensional space for rendering on the display 170.

According to one embodiment of the disclosure, the state sensing logic 194 may generate a rendering of the current physical state of the device 120, based on heuristics or run-time analytics. For example, the state sensing logic 194 may be configured in accordance with machine-learning techniques to access the data repository 190 with pre-stored data (e.g., images, etc.) pertaining to different regions of the device 120 in which reflected light from core fibers have previously experienced similar or identical wavelength shifts. From the pre-stored data, the current physical state of the device 120 may be rendered. Alternatively, as another example, the state sensing logic 194 may be configured to determine, during run-time, changes in the physical state of each region of the optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the optical fiber 135 to the wavelength shift generated by a sensor of the center core fiber at the same cross-sectional region. It is contemplated that other processes and procedures may be performed to utilize the wavelength shifts as measured by sensors along each of the core fibers within the optical fiber 135 to render appropriate changes in the physical state of the device 120, especially to enable guidance of the device 120 when positioned within the patient and at a desired destination within the body.

It is contemplated that other processes and procedures may be performed to utilize the wavelength shifts as measured by sensors along each of the core fibers within the optical fiber 135 to render appropriate changes in the physical state of the probe 120, especially to enable guidance of the probe 120 when positioned within the patient and at a desired destination within the body. For example, wavelength shifts as measured by sensors along one or more of the core fibers may be based on physical states or condition of the probe 120 other than or in addition to longitudinal strain experienced by the device 120. Alternative or additional physical states may include one or more of torsional strain, temperature, motion, oscillations, pressure, or fluid flow adjacent the elongate medical device.

Figure 2:
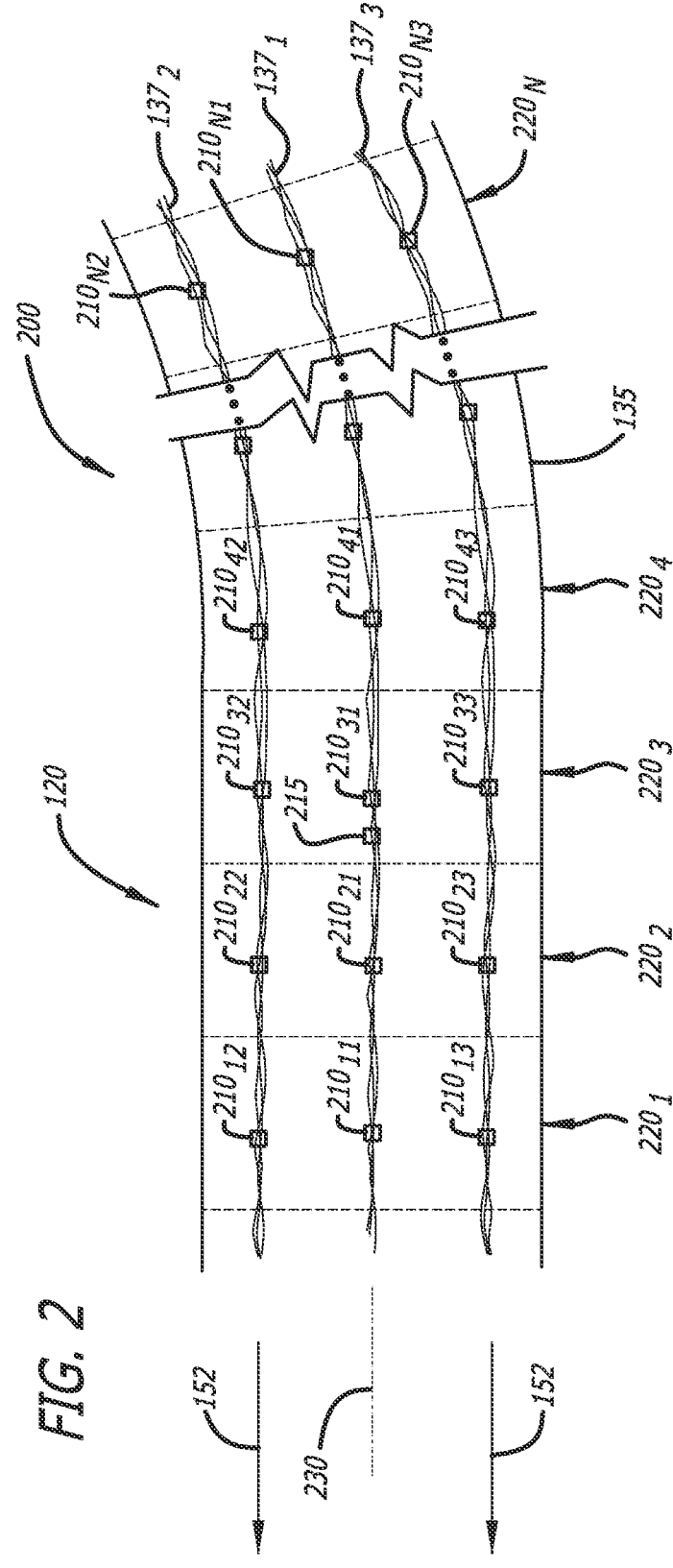
FIG. 2 is an exemplary embodiment of a structure of a section of the elongate medical device of FIG. 1, in accordance with some embodiments.

Referring to FIG. 2, an exemplary embodiment of a structure of a section of the optical fiber of FIG. 1 is shown in accordance with some embodiments. The optical fiber section 200 of the optical fiber 135 depicts certain core fibers 137₁-137_M (M>2, M=4 as shown, see FIG. 3A) along with the spatial relationship between sensors (e.g., reflective gratings) 210₁₁-210_NM (N>2; M>2) present within the core fibers 137₁-137_M, respectively. As noted above, the core fibers 137₁-137_M may be collectively referred to as "the core fibers 137."

As shown, the section 200 is subdivided into a plurality of cross-sectional regions 220₁-220_N, where each cross-sectional region 220₁-220_N corresponds to reflective gratings 210₁₁-210₁₄ . . . 210_N1-210_N4. Some or all of the cross-sectional regions 220₁ . . . 220_N may be static (e.g., prescribed length) or may be dynamic (e.g., vary in size among the regions 220₁ . . . 220_N). A first core fiber 137₁ is positioned substantially along a center (neutral) axis 230 while core fiber 137₂ may be oriented within the cladding of the optical fiber 135, from a cross-sectional, front-facing perspective, to be position on "top" the first core fiber 137₁. In this deployment, the core fibers 137₃ and 137₄ may be positioned "bottom left" and "bottom right" of the first core fiber 137₁. As examples, FIGS. 3A-4B provides illustrations of such.

Referencing the first core fiber 137₁ as an illustrative example, when the device 120 (see FIG. 1) is operative, each of the reflective gratings 210₁-210_N reflects light for a different spectral width. As shown, each of the gratings 210₁ᵢ-210_Ni (1<i<M) is associated with a different, specific spectral width, which would be represented by different center frequencies of $f_1 \ldots f_N$, where neighboring spectral widths reflected by neighboring gratings are non-overlapping according to one embodiment of the disclosure.

Herein, positioned in different core fibers 137₂-137₃ but along at the same cross-sectional regions 220-220_N of the optical fiber 135, the gratings 210₁₂-210_N2 and 210₁₃-210_N3 are configured to reflect incoming light at the same (or substantially similar) center frequency. As a result, the reflected light returns information that allows for a determination of the physical state of the core fibers 137 (and the device 120) based on wavelength shifts measured from the returned, reflected light about the center frequency. In particular, strain (e.g., compression or tension) applied to the optical fiber 135 (e.g., at least core fibers 137₂-137₃) results in wavelength shifts associated with the returned, reflected light. Based on different locations, the core fibers 137₁-137₄ experience different types and/or degrees of strain based on angular path changes as the device 120 advances in the patient.

For example, with respect to the multi-core optical fiber section 200 of FIG. 2, in response to angular (e.g., radial) movement of the device 120 is in the left-veering direction, the fourth core fiber 137₄ (see FIG. 3A) of the optical fiber 135 with the shortest radius during movement (e.g., core fiber closest to a direction of angular change) would exhibit compression (e.g., forces to shorten length). At the same time, the third core fiber 137₃ with the longest radius during movement (e.g., core fiber furthest from the direction of angular change) would exhibit tension (e.g., forces to increase length). As these forces are different and unequal, the reflected light from reflective gratings 210_N2 and 210_N3 associated with the core fiber 137₂ and 137₃ will exhibit different changes in wavelength. The differences in wavelength shift of the reflected light signals 150 can be used to extrapolate the physical configuration of the device 120 by determining the degrees of wavelength change caused by compression/tension for each of the periphery fibers (e.g., the second core fiber 137₂ and the third core fiber 137₃) in comparison to the wavelength of the reference core fiber (e.g., first core fiber 137₁) located along the neutral axis 230 of the optical fiber 135. These degrees of wavelength change may be used to extrapolate the physical state of the device 120. The reflected light signals 150 are reflected back to the console 110 via individual paths over a particular core fiber 137₁-137_M.

Figure 3A:
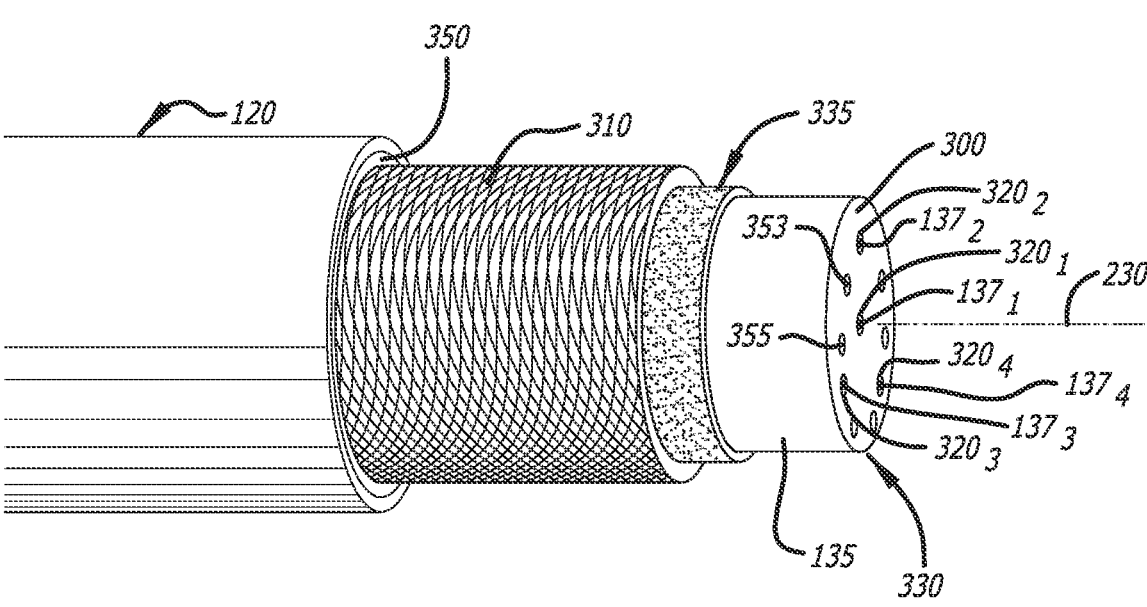
FIG. 3A illustrates an embodiment of the elongate medical device of FIG. 1, in accordance with some embodiments.

Referring to FIG. 3A, a first exemplary embodiment of the probe of FIG. 1 supporting both an optical and electrical signaling is shown in accordance with some embodiments. Herein, the probe 120 features a centrally located multi-core optical fiber 135, which includes a cladding 300 and a plurality of core fibers 137₁-137_M (M>2; M=4) residing within a corresponding plurality of lumens 320₁-320_M. While the multi-core optical fiber 135 is illustrated within four (4) core fibers 137₁-137₄, a greater number of core fibers 137₁-137_M (M>4) may be deployed to provide a more detailed three-dimensional sensing of the physical state (e.g., shape, etc.) of the multi-core optical fiber 135 and the probe 120 deploying the optical fiber 135.

In some embodiments, the multi-core optical fiber 135 is encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the probe 120, as a greater spacing may provide a lesser rigidity, and thereby, a more pliable probe 120.

Figure 3B:
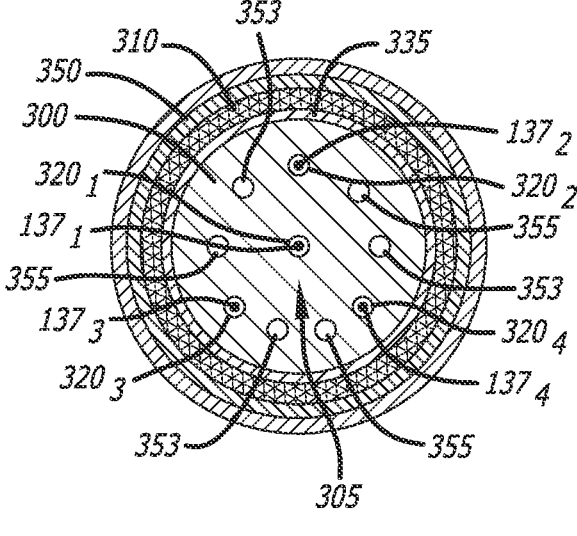
FIG. 3B is a cross sectional end view of the elongate medical device of FIG. 3A, in accordance with some embodiments.

According to this embodiment of the disclosure, as shown in FIGS. 3A-3B, the core fibers $137_1$-$137_4$ include (i) a central core fiber $137_1$ and (ii) a plurality of periphery core fibers $137_1$-$137_4$, which are maintained within lumens $320_1$-$320_4$ formed in the cladding 300. According to one embodiment of the disclosure, one or more of the lumen $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the multi-core optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_1$-$320_4$ each formed within different areas of the cladding 300 radiating from the first neutral axis 230. In general, the core fibers $137_1$-$137_4$, exclusive of the central core fiber $137_1$, may be positioned at different areas within a cross-sectional area 305 of the cladding 300 to provide sufficient separation to enable three-dimensional sensing of the multi-core optical fiber 135 based on changes in wavelength of incident light propagating through the core fibers $137_1$-$137_4$ and reflected back to the console for analysis.

For example, where the cladding 300 features a circular cross-sectional area 305 as shown in FIG. 3B, the core fibers $137_1$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_1$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3A-3B, operating as the conductive medium for the probe 120, the braided tubing 310 may provide mechanical integrity to the multi-core optical fiber 135 and may also operate as a conductive pathway for electrical signals. The cladding 300 and the braided tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both for the cladding 300 and the braided tubing 310, as shown.

Figure 4A:
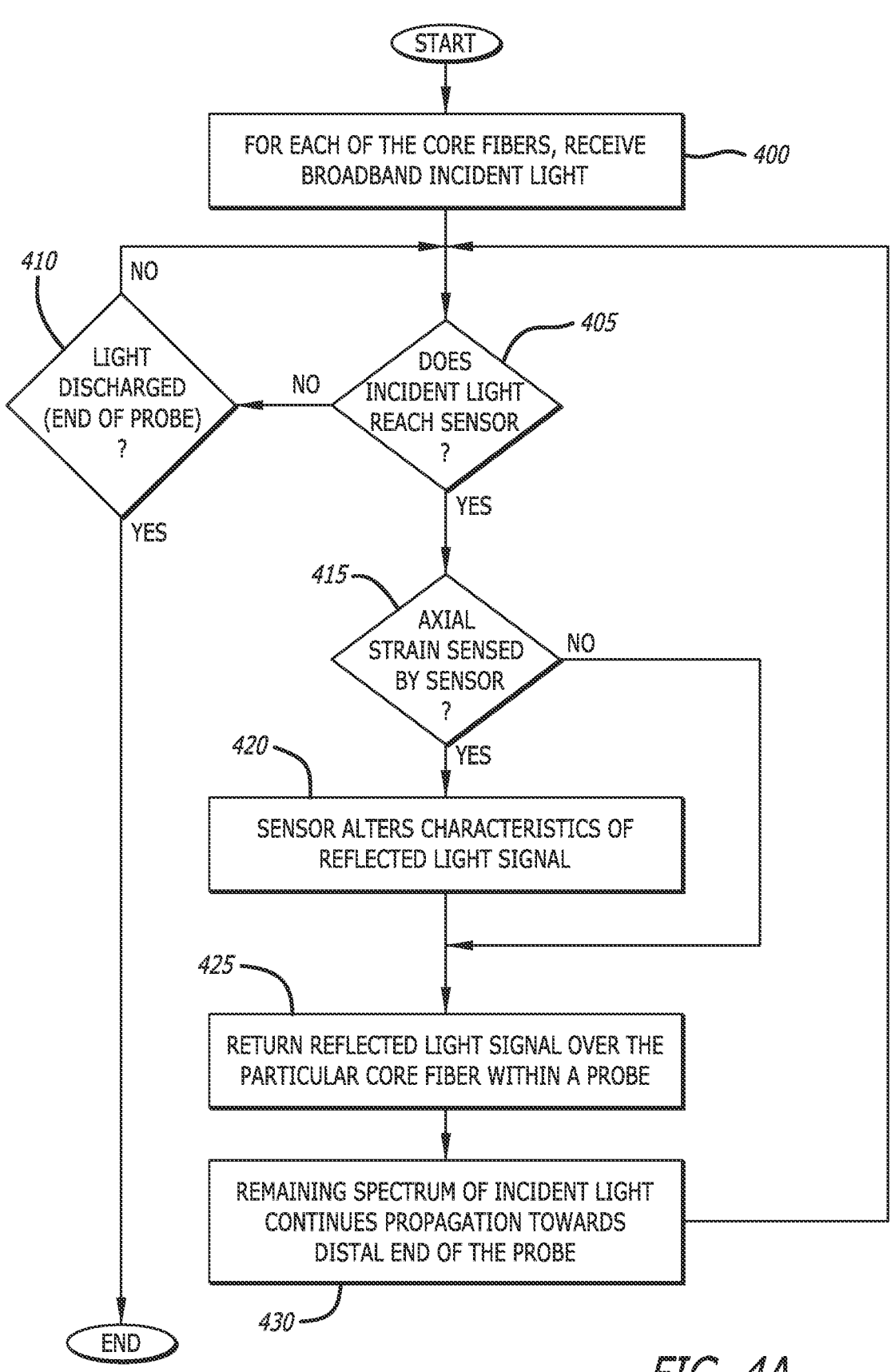
FIGS. 4A-4B are flowcharts of the methods of operations conducted by the medical system of FIG. 1 to achieve optical three-dimensional shape sensing, in accordance with some embodiments.
Figure 4B:
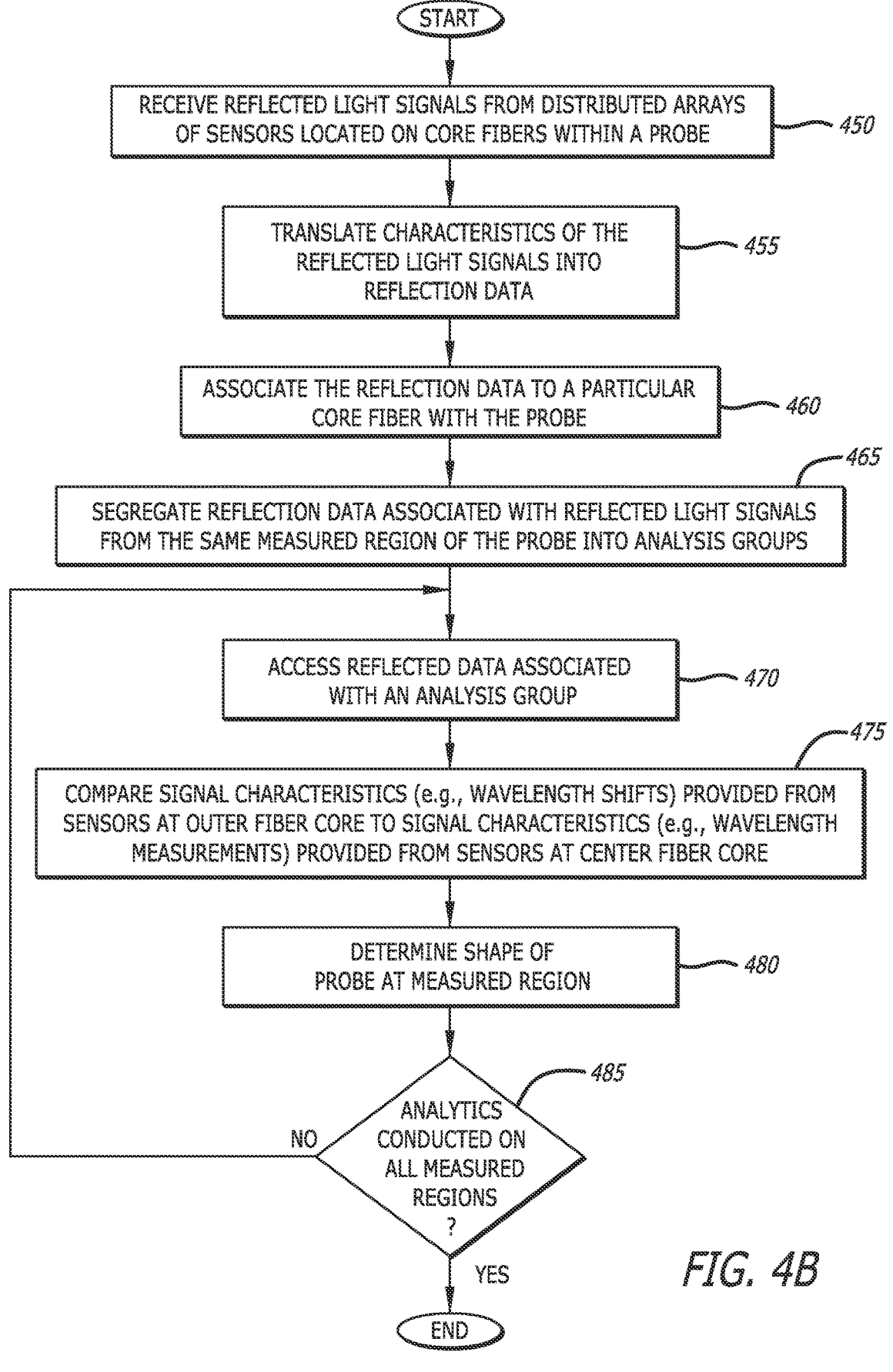

Referring to FIGS. 4A-4B, flowcharts of methods of operations conducted by the medical device system of FIG. 1 to achieve optic three-dimensional shape sensing are shown in accordance with some embodiments. The first micro-lumen is coaxial with the central axis of the probe.

The first micro-lumen is configured to retain a center core fiber. Two or more micro-lumen, other than the first micro-lumen, are positioned at different locations circumferentially spaced along the circumferential edge of the probe. For example, two or more of the second plurality of micro-lumens may be positioned at different quadrants along the circumference edge of the probe.

Furthermore, each core fiber includes a plurality of sensors spatially distributed along its length between at least the proximal and distal ends of the probe. This array of sensors is distributed to position sensors at different regions of the core fiber to enable distributed measurements of strain throughout the entire length or a selected portion of the probe. These distributed measurements may be conveyed through reflected light of different spectral widths (e.g., specific wavelength or specific wavelength ranges) that undergoes certain wavelength shifts based on the type and degree of strain, including oscillations of the strain.

According to one embodiment of the disclosure, as shown in FIG. 4A, for each core fiber, broadband incident light is supplied to propagate through a particular core fiber (block 400). Unless discharged, upon the incident light reaching a sensor of a distributed array of sensors measuring strain on a particular core fiber, light of a prescribed spectral width associated with the first sensor is to be reflected back to an optical receiver within a console (blocks 405-410). Herein, the sensor alters characteristics of the reflected light signal to identify the type and degree of strain on the particular core fiber as measured by the first sensor (blocks 415-420). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the probe (blocks 425-430). The remaining spectrum of the incident light may encounter other sensors of the distributed array of sensors, where each of these sensors would operate as set forth in blocks 405-430 until the last sensor of the distributed array of sensors returns the reflected light signal associated with its assigned spectral width and the remaining spectrum is discharged as illumination.

Referring now to FIG. 4B, during operation, multiple reflected light signals are returned to the console from each of the plurality of core fibers residing within the corresponding plurality of micro-lumens formed within a probe. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 450-455). The reflection data classification logic is configured to identify which core fibers pertain to which reflection data and segregate reflection data provided from reflected light signals pertaining to a particular measurement region (or similar spectral width) into analysis groups (block 460-465).

Each analysis group of reflection data is provided to sensing logic for analytics (block 470). Herein, the sensing logic compares wavelength shifts at each outer core fiber with the wavelength shift at the center core fiber positioned along central axis and operating as a neutral axis of bending (block 475). From this analytics, on all analytic groups (e.g., reflected light signals from sensors in all or most of the core fibers), the sensing logic may determine the shape the core fibers have taken in three-dimensional space, from which the sensing logic can determine the current physical state of the probe in three-dimensional space (blocks 480-485).

Figure 5:
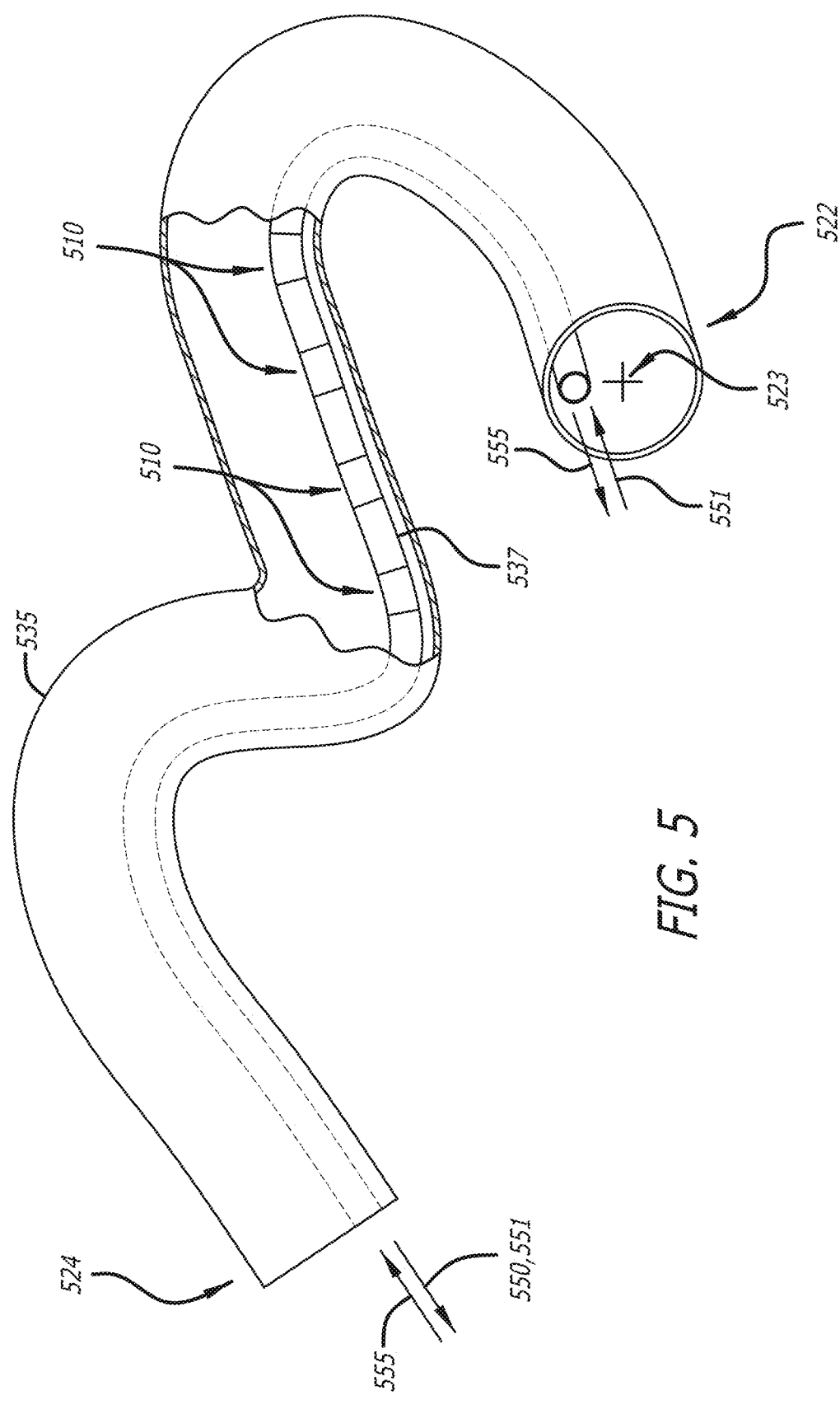
FIG. 5 is perspective illustration another embodiment of an optical fiber having a single core fiber disposed offset from a central axis of the optical fiber, in accordance with some embodiments.

Referring to FIG. 5, illustrates a second exemplary embodiment of an optical fiber 535 that can, in certain respects, resemble components of the optical fiber 135 described in connection with FIGS. 1-3B. It will be appreciated that all the illustrated embodiments may have analogous features. Accordingly, like features are designated with like reference numerals, with the leading digits of "5." For instance, the core fibers are designated as "137" in FIGS. 1-3B, and analogous core fibers are designated as "537" in FIG. 5. Relevant disclosure set forth above regarding similarly identified features thus may not be repeated hereafter. Moreover, specific features of the optical fiber 135 and related components shown in FIGS. 1-3B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the optical fiber 535 of FIG. 5. Any suitable combination of the features, and variations of the same, described with respect to the optical fiber 135 and components illustrated in FIGS. 1-3B can be employed with the optical fiber and components of FIG. 5, and vice versa.

The optical fiber 535 includes a single core fiber 537 having a number (e.g., at least 1, 5, 10, 20, 40 or more) of sensors (e.g., reflective gratings) 510 disposed along a length of the optical fiber 535. The single core fiber 537 is disposed radially offset from a central axis 523 of the optical fiber 535. The optical fiber 535 is configured for insertion within the vasculature of the patient, such as along with or as part of the device 120. In some embodiments, the optical fiber 535 may disposed within a lumen of a catheter and in some embodiments, the optical fiber 535 may be embedded within or extend along a wall of the catheter.

The optical fiber 535 is generally configured to determine a shape or movement (i.e., changing shape) of the optical fiber 535 or portion thereof which by association may include the device 120 or portion thereof. The single core fiber 537 is disposed radially offset from a central axis 523 of the optical fiber 535. As such, bending (or otherwise changing a curvature of) the optical fiber 535 may generate a strain of the core fiber 537, where the strain is detectable via the sensors 510 disposed along a length of the core fiber 537.

The core fiber 537 may also be configured to (i) project an excitation light 551 distally away from the distal end 522 of the optical fiber 535 and (ii) receive an excitation light signal 555 via the distal end 522. In some embodiments, the excitation light 551 may be an illuminating light and the excitation light signal 555 may include an image of an anatomical element of the patient body or other object adjacent the distal end 522.

The sensors 510 or a subset thereof may be configured to determine longitudinally compressive strain along a portion of the optical fiber 535. For example, a subset of sensors adjacent the distal tip 522 may be configured to detect (i) engagement/contact with check valves of a vein or (ii) abutment with other anatomical elements, such as a blood vessel wall, for example.

In some embodiments, the orientation (i.e., angular position) of the core fiber 537 may be known. For example, the device 120 may include a feature (e.g., an indicium) indicating the angular position of the core fiber 537. For example, the device 120 may be configured so that, when the indicium is vertically oriented, the core fiber 537 is oriented at the 12 o-clock position. As such, during use, the clinician may rotate device 120 about its longitudinal axis and thereby, correspondingly orient the single core fiber 537 in a desired direction.

Figure 6A:
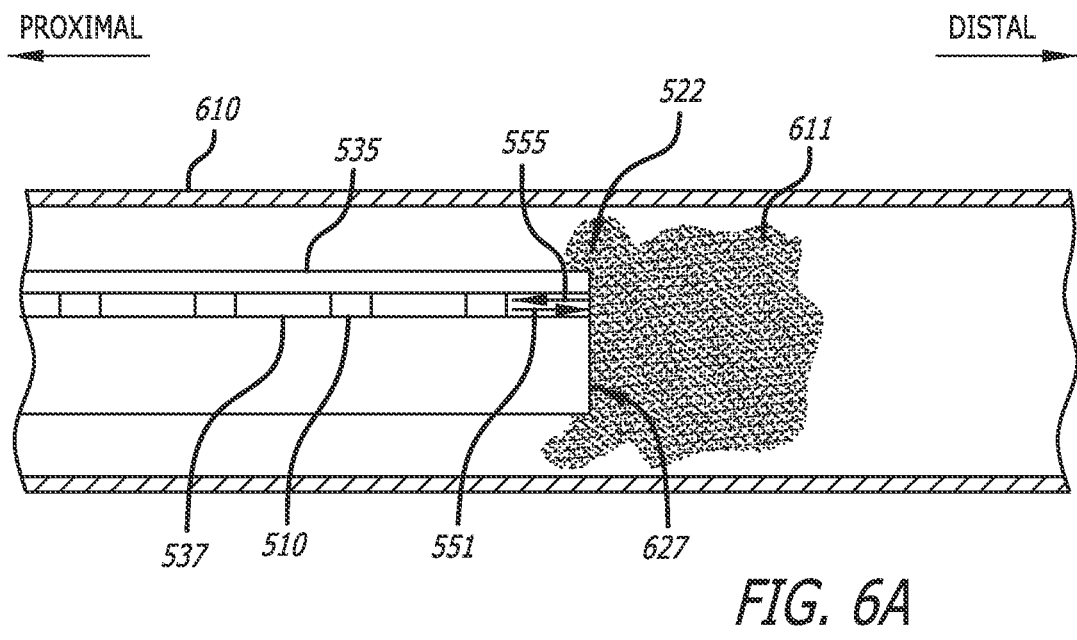
FIG. 6A illustrates an implementation of the optical fiber of FIG. 5 determining a pH of a blood, in accordance with some embodiments.

FIG. 6A illustrates a first implementation of the optical fiber 535 in combination with the state sensing logic 194 determining a pH of a solution. FIG. 6A shows the optical fiber 535 disposed within a blood vessel 610 such that the distal end 522 is in contact with the blood 611. In some embodiments, the optical fiber 535 may include a coating 627 disposed across a distal face of the optical fiber 535. The coating 627 may be configured to define a characteristic of the excitation light signal 555 based on a pH of a solution (e.g., the blood 611) in contact with the coating 627. In some embodiments, the characteristic of the excitation light signal 555 may be a color. By way of one example, the coating 627 may be configured to function similar to a litmus paper that changes color in accordance with a pH of a solution in contact with the litmus paper. In some embodiments, the coating 627 may be applied to a surface of the device 120 other than the optical fiber 535 directly.

In some embodiments, the system may determine a pH of a solution in contact with the coating 627. In some embodiments of use, the solution may be the blood 611, while in other embodiments, the solution may be some other solution, such as an infusate, or urine, for example. In some embodiments, the state logic 194 may project the excitation light 555 distally along the single core fiber 537 so as to optically excite (e.g., illuminate) the coating 627. The state logic 194 may receive the excitation light signal 555 including a characteristic of the excitation light signal 555 that is based on the pH. The state logic 194 may further extract pH data from the excitation light signal 555 and communicate the pH to the user, such as via the display 170, for example.

Figure 6B:
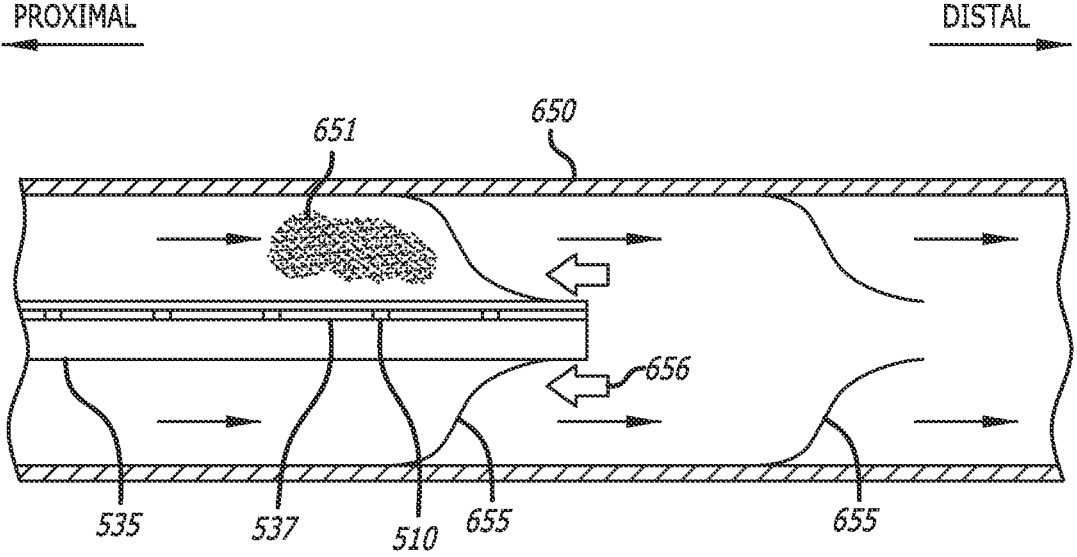
FIG. 6B illustrates an implementation of the optical fiber of FIG. 5 determining engagement of the optical fiber with the check valves of a vein, in accordance with some embodiments.

FIG. 6B illustrates a second implementation of the optical fiber 535 in combination with the state sensing logic 194 identifying check valves along a blood vessel, such as are present along a vein. FIG. 6B shows a vein 650 having venous blood 651 flowing through check valves 655. The optical fiber 535 is shown inserted into the vein 650 in the direction of flow of the venous blood 651. The optical fiber 535 is further shown inserted through one of the check valves 655.

During advancement of the optical fiber 535 along the vein 650, the optical fiber 535 may engage/contact the check valve 655 such that the check valve 655 exerts a force 656 onto the optical fiber 535. The optical fiber 535 experiences a longitudinally directed compressive strain as a result of the exerted force 656. The sensors 510, in turn, may define the varying reflected light signals based on the compressive strain of the optical fiber 535 induced by the exerted force 656.

The state sensing logic 194 may receive electrical signals related the reflected light signals during the insertion process of the optical fiber 535. As the optical fiber 535 engages the check valve 655 during insertion, the electrical signals may indicate a change in the reflected light signals based on the compressive strain resulting from engagement of the optical fiber 535 with the check valve 655 and define present engagement data therefrom. For example, during insertion the state sensing logic 194 may determine a first level of compressive strain as the optical fiber is advanced between adjacent check valves 655 and then determine an increased second level (e.g., a spike) of compressive strain as the optical fiber 535 engages/contacts each check valve 655. In some embodiments, the state sensing logic 194 compare a present difference in magnitude between the second level of compressive strain and the first level of compressive strain with a difference in magnitude stored in memory. As a result of the comparison, the state sensing logic 194 may identify check valves 655 along a blood vessel.

According to a similar implementation, in some instances during insertion of the optical fiber 535, the distal end 522 may abut other anatomical elements, such as a blood vessel wall, for example. In some instances, continued insertion may cause harm to the patient. As such, the state sensing logic 194 may identify the abutment and alert the user to prevent the harm. The state sensing logic 194 may receive electrical signals related the reflected light signals during the insertion process of the optical fiber 535. When the optical fiber 535 abuts an anatomical element during insertion, the electrical signals may indicate a change in the reflected light signals based on the compressive strain resulting from the abutment and define present abutment data therefrom. For example, during insertion the state sensing logic 194 may determine an increased level (e.g., a spike) of compressive strain when the optical fiber 535 abuts the anatomical element. In some embodiments, the state sensing logic 194 compare the present increased level of compressive strain with a safety limit stored in memory. As a result of the comparison, the state sensing logic 194 may identify the abutment and provide an alert to the user.

Figure 6C:
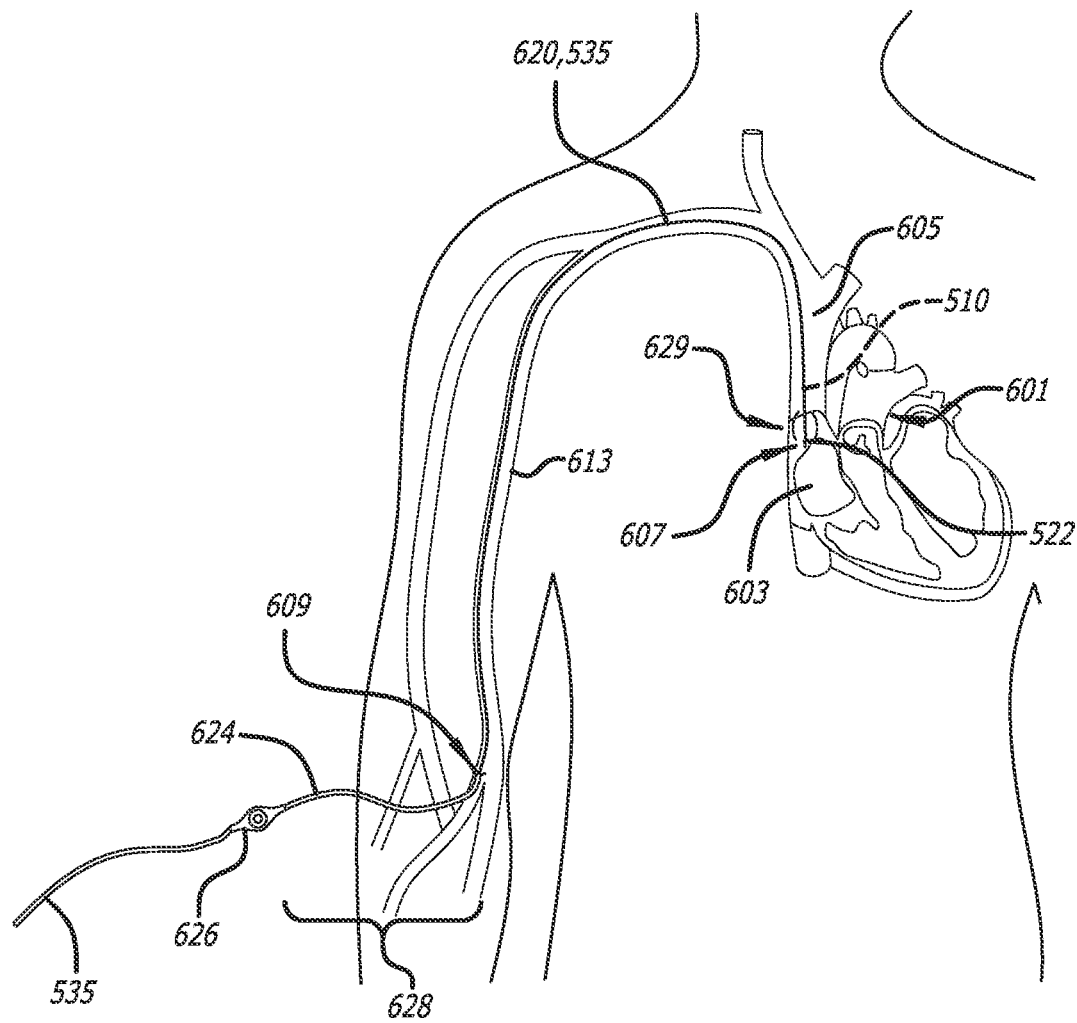
FIG. 6C illustrates an implementation of the optical fiber of FIG. 5 determining an insertion length of the optical fiber, in accordance with some embodiments.

FIG. 6C illustrates a third implementation of the optical fiber 535 in combination with the state sensing logic 194 determining the location of a cavoatrial junction (CAJ) of the patient with respect to an insertion site of a catheter, such as a peripherally inserted central catheter (PICC), for example. In other words, the state sensing logic 194 in combination with the optical fiber 535 may determine a length of a vascular pathway from the insertion site to the CAJ. FIG. 6C shows a vascular pathway 613 extending between an insertion site 609 and a heart 601. Also shown is the CAJ 607 disposed between the superior vena cava 605 and the right atrium 603. A PICC 624 having a hub 626 is inserted into the vascular pathway 613. An excess length 628 of the PICC 624 is also shown extending between the insertion site 609 and the hub 626. The optical fiber 535 is also inserted with the vascular pathway 613 so that the distal end 522 is disposed adjacent the CAJ 607.

In some instances, it may be beneficial to shorten/trim the PICC 624 so as to minimize the excess length 628. In accordance with one exemplary implementation, the optical fiber 535 which may be incorporated into a guidewire may be inserted into the vascular pathway 613 until a fluctuating motion of the optical fiber is detected by the sensors 510 of the optical fiber 535 located adjacent the distal end 622. The fluctuating motion may be caused by oscillating motion of anatomical elements adjacent the CAJ 607, such as fluctuating blood pressure or flow, or oscillating motion of heart tissue or tissue adjacent the heart, for example. In other words, the state sensing logic 194 may be configured to provide notification to the user when the optical fiber 535 is sufficiently inserted to locate the distal end 522 adjacent the CAJ 607.

The state sensing logic 194 may then determine an insertion length of the optical fiber 535 disposed within the vascular pathway 613. According to one exemplary implementation, the state sensing logic 194 may determine the insertion length via the blood temperature sensed along the insertion length versus to the room temperature sensed along an excess length of the optical fiber 535 disposed outside of the vascular pathway 613. In some embodiments, the state sensing logic 194 may communicate the insertion length to the user via the display 170. The user may then trim the PICC in accordance with the determined insertion length. The user may also thread the PICC 624 along the optical fiber 535 to advance the PICC 624 to the CAJ 607. As may be appreciated by one or ordinary skill, the state sensing logic 194 may utilize any other sensing capabilities of the optical 535 described above to locate the distal end 522 adjacent the CAJ 607 and/or determine the insertion length.

Figures 6D, 6E:
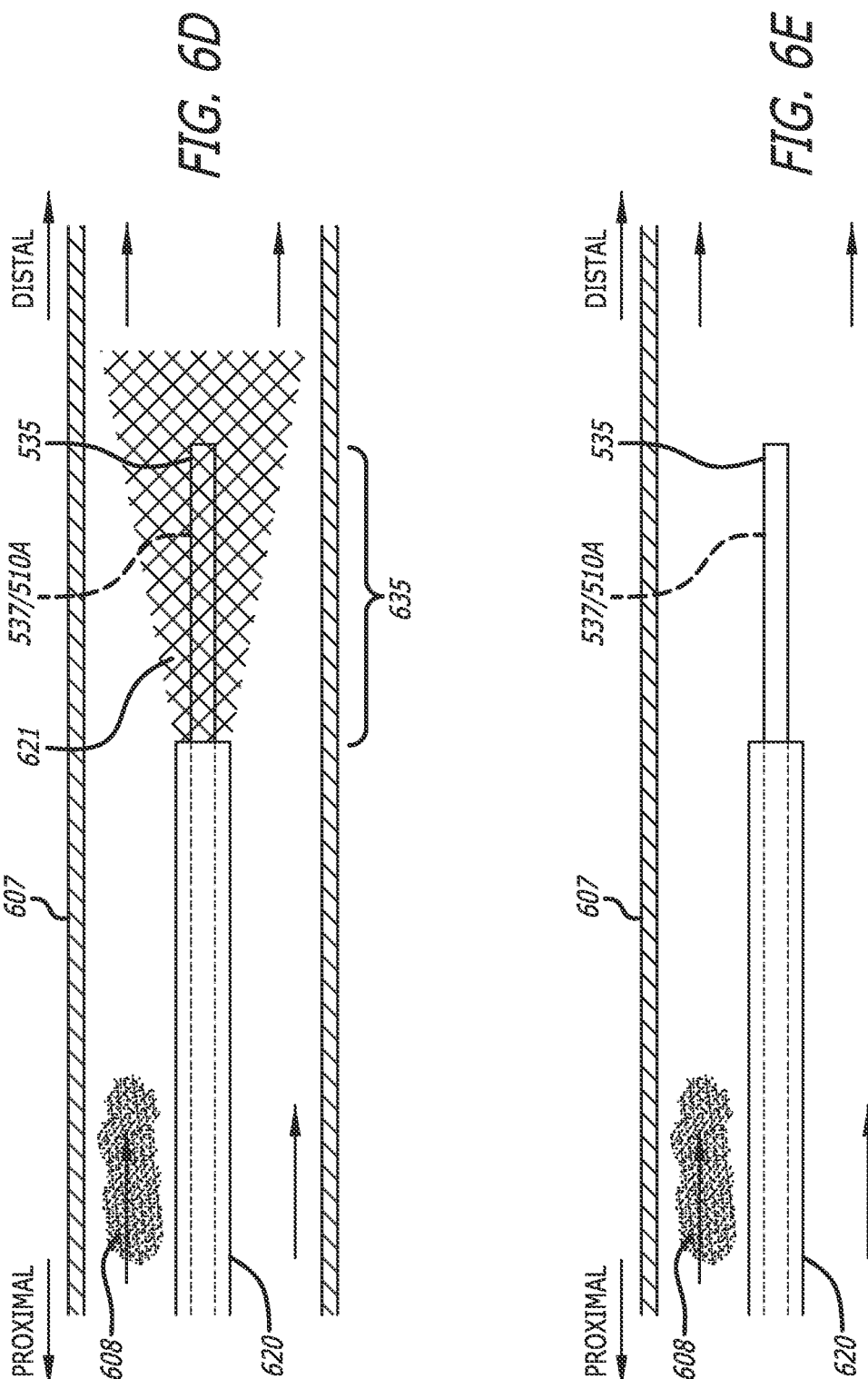
FIGS. 6D-6E illustrate an implementation of the optical fiber of FIG. 5 determining parameters of infusate delivery, in accordance with some embodiments.

FIGS. 6D-6E illustrate a fourth implementation of the optical fiber 535 in combination with the state sensing logic 194 determining parameters of an infusate delivery. As an infusate is delivered to a blood vessel via a catheter, the infusate is generally mixed with the blood downstream of the point of infusion (e.g., the distal end of the catheter). As the infusate may have a temperature different that the blood, the temperature of the blood portion having infusate mixed therewith (i.e., the blood portion downstream of the infusion point) may be measurably different than the temperature of the blood portion having no infusate mixed therewith (i.e., the blood portion upstream of the infusion point). As such, delivery parameters of the infusate may be determined, such as the starting and stopping of delivery.

In the illustrated embodiment, at least a subset of the sensors 510 of the optical fiber 535 are configured to detect temperature, e.g., determine a temperature of a substance, such as blood 608, for example, adjacent the optical fiber 535 at the locations of the respective sensors 510. In some embodiments, determining a temperature may include the sensors 510 detecting a temperature induced strain of the optical fiber 535 due to thermal expansion/contraction.

FIG. 6D illustrates a catheter 620 delivering an infusate 621 to a blood vessel 607 and FIG. 6E illustrates the catheter 620 not delivering an infusate 621 to the blood vessel 607. The optical fiber 535 extends along the catheter 620 (e.g., inserted within a lumen of the catheter 620) such that a section 635 of the optical fiber 535 along with a subset 510A of sensors 510 extend beyond the catheter 620. Each sensor 510 of the subset 510A are configured to determine temperature. As such, the subset 510A of sensors 510 sense a temperature of a mixture of infusate 621 and blood 608 during delivery of the infusate (FIG. 6C). Similarly, the subset 510A of sensors 510 sense a temperature of the blood 608 only during non-delivery of the infusate (FIG. 6D).

In some embodiments, the state sensing logic 194 may receive a first reflected light signal from the subset 510A during non-delivery of the infusate 621, the first reflected light signal based on the first present temperature of the blood 608. The state sensing logic 194 may receive a second reflected light signal from subset 510A during delivery of the infusate 621, the second reflected light signal based on a present second temperature of the blood 608 mixed with the infusate 621. In some embodiments, the state sensing logic 194 may compare the first and second present temperatures with a temperature limit stored in the non-transitory computer-readable storage medium and as a result of the comparison determine when the infusate 621 is delivered versus non-delivered.

Similarly, the state sensing logic 194 may determine when delivery is initiated and terminated, where initiating and terminating the delivery of the infusate defines a flushing event. In such embodiments, the state sensing logic 194 may determine a number and or frequency of flushing events. In a similar fashion, as the delivery rate of infusate may be known, the state sensing logic 194 may determine a delivery volume of infusate. In an alternative implementation, the delivery of the infusate may include individually infused known volumes (e.g., volumes delivered by multiple syringes). In such an implementation, the state sensing logic 194 may count the number of individually infused known volumes and determine therefrom a total infused volume of infusate.

Figures 6F, 6G:
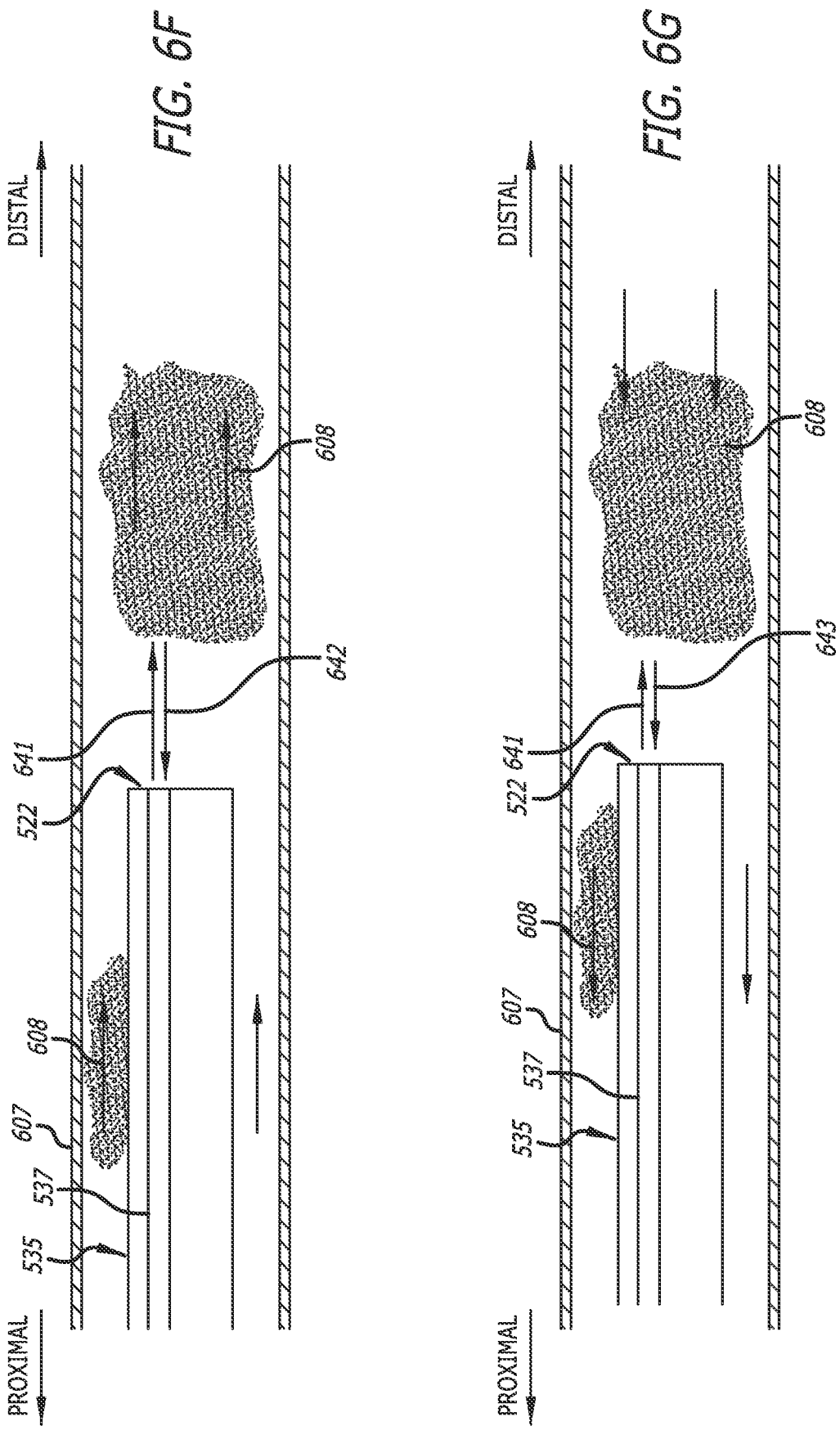
FIGS. 6F-6G illustrate an implementation of the optical fiber of FIG. 5 determining blood flow parameters within a blood vessel based a wavelength shift between a light projected onto and a light reflected off of particles within the blood, in accordance with some embodiments.

FIGS. 6F-6G illustrate a fifth implementation of the optical fiber 535 in combination with the state sensing logic 194 determining blood flow parameters based on reflections of incident light that are shifted toward the red or blue spectrum. The optical fiber 535 may be advanced along a blood vessel in the same direction as the blood flow or in the opposite direction to the blood flow. In accordance with the doppler effect, reflections of incident light projected onto particles within the blood may shift toward the red spectrum (i.e., longer wavelengths) when the blood is flowing away from the light source. Conversely, reflections of incident light projected onto particles within the blood may shift toward the blue spectrum (i.e., shorter wavelengths) when the blood is flowing toward from the light source. As such, an analysis of the reflected light may indicate a direction of blood flow. In a similar fashion (i.e., via the doppler effect), the state sensing logic 194 may also determine a velocity of the blood 608 flow in either the distal direction or proximal direction with respect to the optical fiber 535.

FIGS. 6F and 6G illustrate the optical fiber 535 inserted within the blood vessel 607 such that a distal end 522 of the optical fiber 535 is disposed within the blood 608 flowing within the blood vessel 607. An incident light 641 is propagated distally along the optical fiber 535 and projected distally away from the distal end 522 into the blood 608, i.e., onto particles within the blood 608. The incident light 641 reflects off of the particles within the blood 608 to generate reflected light that is received by the optical fiber 535 and propagated proximally back along the optical fiber 535.

FIG. 6F illustrates a first instance, where the blood 608 is flowing in a distal direction with respect to the optical fiber 535. As such, the incident light 641 is projected onto blood particles that are moving away from the distal end 522 generating reflected light 642 that has shifted toward the red spectrum with respect to the incident light 641.

FIG. 6G illustrates a second instance, where the blood 608 is flowing in a proximal direction with respect to the optical fiber 535. As such, the incident light 641 is projected onto blood particles that are moving toward the distal end 522 generating reflected light 643 that has shifted toward the blue spectrum with respect to the incident light 641.

The state sensing logic 194 may receive electrical signals related to the reflected light propagated proximally along the optical fiber 535, where the electrical signals indicate a wavelength of the reflected light. In some embodiments, the state sensing logic 194 may compare the present wavelength of the reflected light with a wavelength of the incident light 641. As a result of the comparison, the state sensing logic 194 may determine (i) that the blood 608 is flowing in a distal direction with respect to the optical fiber 535 or (ii) that the blood 608 is flowing in a proximal direction with respect to the optical fiber 535. In some embodiments, the state sensing logic 194 may compare the present wavelength of the reflected light with a wavelength of the incident light 641 and determine therefrom a blood flow velocity.

Figure 6H:
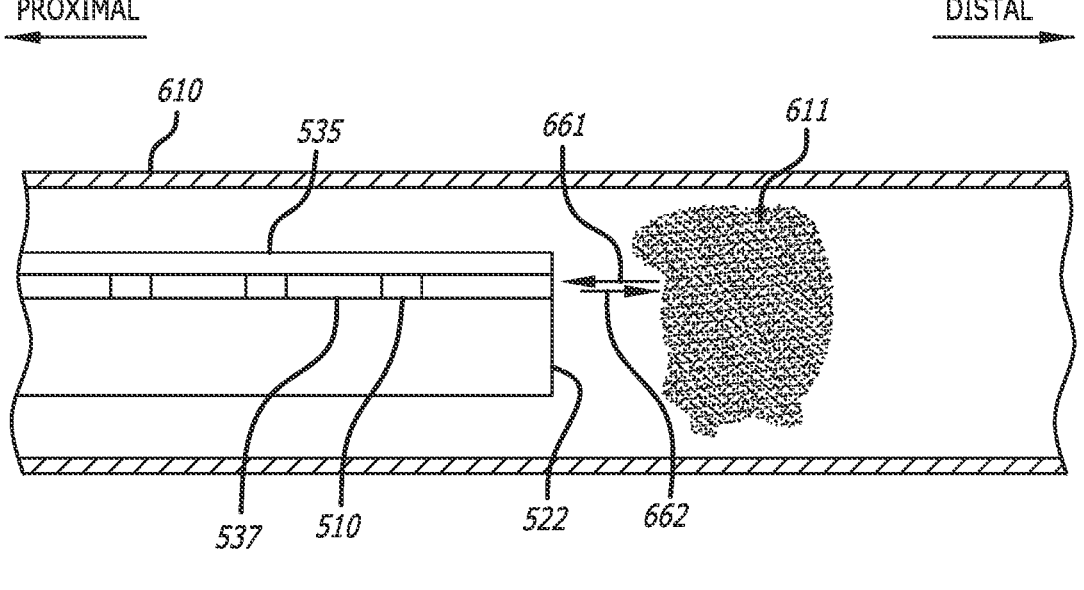
FIG. 6H illustrates an implementation of the optical fiber of FIG. 5 determining an oxygen level of blood, in accordance with some embodiments.

FIG. 6H illustrates a sixth implementation of the optical fiber 535 in combination with the state sensing logic 194 determining an oxygen level of the blood. FIG. 6H shows the optical fiber 535 disposed within the blood vessel 610 such that the distal end 522 is in contact with the blood 611. An excitation light 661 is projected away from the distal end 522 of the optical fiber 535 into the blood 611. The excitation light 661 may comprise wavelengths consistent with generating a return light signal 662 consistent with an oxygen level (oxygen saturation) of the blood 611. The state sensing logic 194 may extract the oxygen level of the blood 611 from the return light signal 662. The state sensing logic 194 may communicate the oxygen level of the blood 611 to the user, such as via the display 170, for example.

Figure 7:
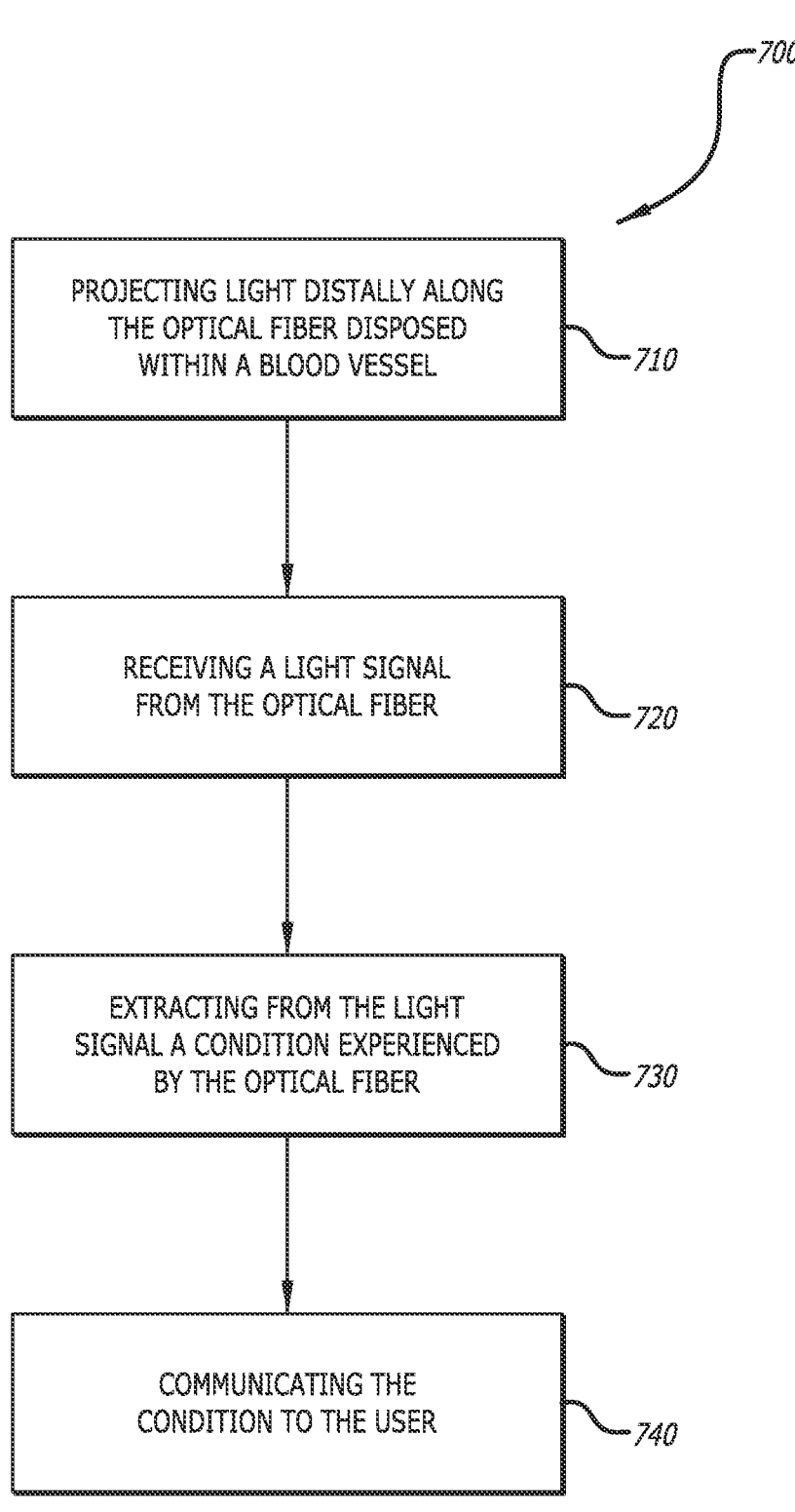
FIG. 7 illustrates a flow chart of a method performed by system, in accordance with some embodiments.

FIG. 7 illustrates a flow chart of a method 700 performed by the medical system 100 that may, according to some embodiments, include all or a subset of the flowing steps or process. The method 700 includes projecting a light distally along an optical fiber of the system (block 710). Projecting the light may include projecting the light away from a distal end of the optical fiber disposed within a blood vessel. In some embodiments, the projected light may include broadband light or specific wavelengths.

The method 700 further includes receiving light signals from the optical fiber (block 720). Receiving the light signal may include receiving the light signal from into the optical fiber via the distal end of the optical fiber. Receiving the light signal may also include receiving reflected light signals defined by sensors disposed along the optical fiber in response to the projected light. In some embodiments, receiving the light signal my include receiving multiple light signals.

The method 700 further includes extracting from the light signal a number of conditions experienced by the optical fiber (block 730). In some embodiments, the number of conditions experienced by the optical fiber may include a damage to the optical fiber. The conditions may also include a compressive force applied longitudinally to the optical fiber resulting from contact of the distal end of the optical fiber with an anatomical element of the patient body. The conditions may also include a shape of the optical fiber which may be defined by a shape of a blood vessel, for example.

In some embodiments, the number of conditions experienced by the optical fiber includes conditions of the patient body that include one or more of a velocity and or direction of blood flow with respect to the optical fiber. The conditions of the patient body may also include a pH of a fluid within the body, such as blood, urine, infusate, or any other bodily fluid. The conditions of the patient body may also include an oxygen level of the blood. The conditions of the patient body may also include a fluctuating motion of the optical fiber as caused by fluctuating blood flow or pressure within a vasculature. The conditions of the patient body may also include a core temperature of the patient.

The method 700 further includes communicating the extracted conditions to a user (block 740). The communication may include information rendered on the display, such as data, an alert, an image, or the like.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical system, comprising:
    an elongate medical device configured for insertion within a blood vessel of a patient, the elongate medical device comprising:

an optical fiber extending along a longitudinal length of the elongate medical device to a distal end of the elongate medical device, the optical fiber having a single core fiber extending along the optical fiber, the single core fiber disposed radially offset from a central axis of the optical fiber, the single core fiber including a plurality of sensors distributed along the longitudinal length, each sensor of the plurality of sensors configured to (i) reflect a light signal of a different spectral width based on received incident light, and (ii) change a characteristic of the reflected light signal based on a state of the optical fiber; and a console including:

a light source optically coupled with the optical fiber via an optical connector;

an optical receiver optically coupled with the optical fiber via the optical connector;

a display;

a processor; and a non-transitory computer-readable medium having stored thereon logic that, when executed by the processor, causes operations including:

projecting via the light source a light distally along the optical fiber;

receiving via the optical receiver the reflected light signal from the plurality of sensors;

processing the reflected light signal by the processor to determine the state of the optical fiber based on the reflected light signal; and communicating the state to a user via the display, wherein the state includes a temperature.

2. The medical system of claim 1, wherein:

the light includes an illuminating light that is propagated distally along the optical fiber and projected distally away from a distal end of the optical fiber, and the operations further include:

projecting via the light source the illuminating light distally along the optical fiber, wherein the illuminating light is projected distally away from a distal of the optical fiber;

receiving via the optical receiver an image light signal that is received at the distal end and propagated proximally along the optical fiber from the distal end, the image light signal pertaining to an anatomical element of the patient;

processing the image light signal to extract image data from the image light signal; and processing the image data to render the image data in a form of an image of the anatomical element on the display.

3. The medical system of claim 1, wherein the elongate medical device includes a catheter, a stylet, a probe, or a guidewire.

4. The medical system of claim 1, wherein:

the state of the optical fiber includes a fluctuating movement of at least a distal portion of the optical fiber, and the operations further include:

processing the reflected light signal to extract present fluctuating movement data from the reflected light signal;

comparing the present fluctuating movement data with one or more fluctuating movement limits stored in the non-transitory computer-readable medium, the one or more fluctuating movement limits pertaining to movement of the distal portion in response to oscillating anatomic motion adjacent a cavoatrial junction of the patient; and determining, as result of the comparing, that the distal end of the optical fiber is disposed adjacent the cavoatrial junction.

5. The medical system of claim 4, wherein:

the state of the optical fiber further includes the temperature of an inserted portion of the optical fiber, and the operations further include:

receiving by the optical receiver one or more reflected light signals from a subset of the plurality of sensors, the subset disposed along the inserted portion;

processing the one or more reflected light signals to extract present temperature data from the one or more reflected light signals; and processing the present temperature data to determine a length of the inserted portion based on the present temperature data.

* * * * *